United States Patent
Miyamoto et al.

(10) Patent No.: US 9,747,685 B2
(45) Date of Patent: Aug. 29, 2017

(54) METHOD AND SYSTEM FOR SKIN CARE CONSULTATION

(71) Applicant: The Procter & Gamble Company, Cincinnati, OH (US)

(72) Inventors: Kukizo Miyamoto, Ashiya (JP); Iri Sato Baran, Tokyo (JP)

(73) Assignee: The Proctor & Gamble Company, Cincinnati, OH (US)

( * ) Notice: Subject to any disclaimer, the term of this patent is extended or adjusted under 35 U.S.C. 154(b) by 387 days.

(21) Appl. No.: 14/496,523

(22) Filed: Sep. 25, 2014

(65) Prior Publication Data
US 2015/0086104 A1   Mar. 26, 2015

Related U.S. Application Data

(60) Provisional application No. 61/882,245, filed on Sep. 25, 2013.

(51) Int. Cl.
*G06K 9/00*   (2006.01)
*G06T 7/00*   (2017.01)
*C12Q 1/68*   (2006.01)

(52) U.S. Cl.
CPC .............. *G06T 7/0012* (2013.01); *C12Q 1/68* (2013.01); *C12Q 1/6883* (2013.01); *C12Q 2600/156* (2013.01); *G06T 2207/30088* (2013.01)

(58) Field of Classification Search
CPC .............. G06Q 10/063; G06Q 10/0637; G06T 7/0012; G06T 7/0028; G06T 7/408; G06T 2207/30088; C12Q 1/68
See application file for complete search history.

(56) References Cited

U.S. PATENT DOCUMENTS

| 6,291,171 | B1 | 9/2001 | Ricciardi |
| 6,571,003 | B1 | 5/2003 | Hillebrand |
| 8,094,186 | B2 | 1/2012 | Fukuoka |
| 8,218,862 | B2 | 7/2012 | Demirli |

(Continued)

FOREIGN PATENT DOCUMENTS

| JP | 2012050406 A | 3/2012 |
| WO | WO02/80755 A | 10/2002 |

(Continued)

OTHER PUBLICATIONS

Baran, "Machine translation of JP 2012050406A", Mar. 15, 2012, Espacenet, p. 1-48.*

(Continued)

*Primary Examiner* — Stephen R Koziol
*Assistant Examiner* — Timothy Choi
(74) *Attorney, Agent, or Firm* — John G. Powell; S. Robert Chuey

(57) ABSTRACT

Described herein are materials and methods for evaluating skin quality and providing customized, concierge skin consultation to consumers. In various aspects, the disclosure includes a method comprising detecting polymorphisms in MMP1, SOD2, and GPX1 from a biological sample, calculating a genetic skin score, comparing the genetic skin score to current skin features, and optionally counseling a consumer regarding a skin care regimen customized to enhance immediate skin quality and/or future skin quality.

14 Claims, 9 Drawing Sheets

(56) References Cited

U.S. PATENT DOCUMENTS

2008/0107320 A1\* 5/2008 Cotton .............. A61B 5/0059
        382/131
2012/0164647 A1  6/2012 Ricciardi
2013/0023058 A1  1/2013 Toumazou et al.

FOREIGN PATENT DOCUMENTS

WO  WO2009/089292 A1  7/2009
WO  WO2013/093407 A   6/2013

OTHER PUBLICATIONS

"International Search Report PCT/US2014/057353 Written Opinion", Priority date: Sep. 25, 2013; mailing date Jan. 9, 2015.\*

Sasaki et al., "Clinical Parameters for Predicting Efficacy and Safety With Nonablative Monopolar Radiofrequency Treatments to the Forehead, Face, and Neck", Jul. 2007, American Society for Aesthetic Plastic Surgery, Aesthetic Surgery Journal, vol. 27, iss. 4, p. 376-387.\*

Miyamoto, K., et al., "Development of new in vivo imaging methodology and system for the rapid and quantitative evaluation of the visual appearance of facial skin firmness", Skin Res.and Technology 2013:19:e525-e531.

Dhawan et al., Knowledge-based Color and Texture Analysis of Skin Image, Annual International Conference of the IEEE Engineering in Medicine and Biology Society, vol. 12, No. 3, 1990, pp. 1289-1290.

Takemae et al., The Evaluating System of Human Skin Surface Condition by Image Processing, Systems, Man, and Cybernetics, 2000 IEEE International Conference, vol. 1, pp. 218-223.

\* cited by examiner

| Weightings Included in Genetic Skin Score | | | |
|---|---|---|---|
| GPX1 | 1 | | |
| MMP1 | 3 | ←—132 | |
| SOD2 | 2 | | |
| | | | |
| 1: Wild (normal), 2: Hetero (mutant), 3: Homo (Mutant) | | | |
| | | | |
| | | | |
| Current Skin Feature Quality Scores | | | |
| | | | |
| Skin Texture | 72 | | |
| Skin Tension | 85 | | |
| Skin Wrinkles | 50 | ←—135 | |
| Skin Spots | 45 | | |
| Skin Radiance | 60 | | |

| | Skin Texture | Skin Tension | Skin Wrinkles | Skin Spots | Skin Radiance |
|---|---|---|---|---|---|
| Predicted Skin Feature Quality Scores | 42.94 | 61.95 | 58.38 | 83.21 | 61.78 |
| Current Skin Feature Quality Scores | 72 | 85 | 50 | 45 | 60 |

METHOD AND SYSTEM FOR SKIN CARE CONSULTATION

FIELD OF THE INVENTION

The present disclosure is directed to systems and methods for evaluating skin quality and consumer consultation.

INCORPORATION BY REFERENCE OF MATERIAL SUBMITTED ELECTRONICALLY

This application contains, as a separate part of disclosure, a Sequence Listing in computer-readable form (filename: 47982_SeqListing.txt; created: Sep. 25, 2013; 1,074 bytes), which is incorporated by reference in its entirety.

BACKGROUND OF THE INVENTION

Understanding a consumer's skin condition or skin quality plays an important role in skin counseling and product selection/recommendation. It is important that a consumer understands the gap between their current skin condition versus its genetic potential or the genetic predisposition of their skin to develop certain undesirable skin imperfections such as, for example, skin wrinkles, skin spottiness, decreased skin firmness, decreased skin radiance, and decrease skin texture. Armed with this information, the consumer can directly, or indirectly with the help of, e.g., manufacturers, retailers, clinicians, and/or dermatologists, make an informed decision on the type of products (including medicament(s)) that could be useful to maximize their skin's potential or as a preventive measure to delay or offset the progress of undesirable skin features.

Generally, consumers rely on information about their skin condition in order to make a decision about the type of products (e.g., skin care, cosmetic, etc.) needed for their particular skin condition. Typically, consumers choose the desired products according to their limited understanding of their skin quality. For example, the consumer might have an impression of their skin quality from a self-assessment. However, it is easy for the consumer to incorrectly assess their skin condition. Another approach has been to use visual or imaging devices, which tend to provide a more accurate assessment of the consumer's skin quality (see Miyomoto, K., et al., Skin Res. & Tech. (2013), 19:e525-e531). These devices have limited value, however, because they can only provide a snapshot of the consumer's skin quality at one point in time. These devices fail to evaluate or predict the consumer's potential skin condition and/or risk of developing skin imperfections.

An improved method of evaluating skin quality and providing meaningful information and tailored skin care selections/recommendations to the consumer is needed. The need also exists for a system for assessing the skin condition for predicting the consumers risk of developing certain skin features, particularly imperfections, in the future.

SUMMARY OF THE INVENTION

In one aspect, described herein is a method of assessing the skin quality of a human subject, the method comprising: determining the presence or absence of polymorphisms in MMP1, SOD2, and GPX1 in a biological sample from the human subject to provide a genetic skin score; and determining a predicted skin feature quality score corresponding to a skin feature selected from the group consisting of skin wrinkles, skin spots, decreased skin tension, decreased skin radiance, and skin texture roughness, by applying a predictive equation to the genetic skin score; wherein the predictive equation corresponds to the skin feature and is determined by a regression analysis of data obtained from a control group comprising members whose ages span at least two decades, at least three decades, at least four decades, or at least five decades, the data comprising: (i) a genetic skin score of each member of the control group, and (ii) a plurality of measurements corresponding to each member of the control group, wherein the plurality of measurements are associated with the skin feature and calculated from an image analysis of a skin surface of each member of the control group; and wherein the predicted skin feature quality score is representative of a risk of the human subject developing the skin feature.

A system capable of performing any of the methods described herein is also provided. For example, in some embodiments, a system for assessing the skin quality of a human subject is provided. The system comprises at least one processor; an interface; and at least one tangible, non-transitory computer readable storage medium storing computer executable instructions that, when executed by the at least one processor, cause the system to: obtain, via the interface, an indication of the presence or absence of polymorphisms in MMP1, SOD2, and GPX1 in a biological sample from the human subject; determine, based on the indication of the presence or absence of polymorphisms in MMP1, SOD2, and GPX1 in the biological sample from the human subject, a genetic skin score; determine a predicted skin feature quality score corresponding to a skin feature selected from a group of skin features consisting of skin wrinkles, skin spots, decreased skin tension, decreased skin radiance, and skin texture roughness by applying a predictive equation corresponding to the skin feature to the genetic skin score, wherein the predictive equation is determined by a regression analysis of data obtained from a control group comprising members whose ages span at least five decades, the data comprising (i) a genetic skin score of each member of the control group, and (ii) a plurality of measurements corresponding to each member of the control group, the plurality of measurements associated with the skin feature and calculated from an image analysis of a skin surface of each member of the control group, and wherein the predicted skin feature quality score is representative of a risk of the human subject developing the skin feature. In some embodiments, the polymorphisms are rs1799750, rs4880, and rs1050450.

Also provided is a system for determining a gap between a predicted skin quality and a current skin quality of a human subject. The system comprises: at least one processor; at least one communications interface; and at least one tangible, non-transitory computer-readable storage medium having stored thereon a skin quality gap evaluator, the skin quality gap evaluator including computer executable instructions that, when executed by the at least one processor, cause the system to: receive, via the at least one communications interface, first data including at least one indication of the presence or absence, in a biological sample from the human subject, of at least one polymorphism in a set of human genes; determine a value indicative of the predicted skin quality of the human subject, the predicted skin quality value of the human subject determined based on the first data and on a correlation of the presence or absence of the at least one polymorphism to a set of skin features indicative of skin quality; receive, via the at least one communications interface, second data including a value indicative of the current skin quality of the human subject, the current skin quality value determined based on an automatic image-analysis of an image of a portion of the skin surface of the human subject, wherein the automatic image-analysis is configured to determine a measurement corresponding to the set of skin features of the portion of the skin surface; determine, based on the predicted skin quality value and the current skin quality value, a magnitude of a gap between the predicted skin quality and the current skin quality of the human subject; and cause an indication of the gap magnitude to be presented at a user interface.

Also described herein is a method of determining, based on a set of skin features corresponding to skin quality of humans, a gap between a predicted skin quality and a current skin quality of a human subject. The method comprises: (a) analyzing at least one skin surface of the human subject to determine at least one measurement indicative of the current skin quality of the human subject, wherein the at least one measurement corresponds to at least one skin feature of the set of skin features; and (b) determining, by a computing device and based on the at least one measurement, a magnitude of a gap between the current skin quality of the human subject and the predicted skin quality of the human subject, the predicted skin quality of the human subject determined based on a presence or absence of at least one polymorphism identified in nucleic acid from a biological sample from the human subject, wherein: each polymorphism of the at least one polymorphism is correlated with affecting one or more skin features of the set of skin features corresponding to skin quality, and the set of skin features corresponding to skin quality includes at least one of skin wrinkles, skin texture roughness, skin spots, decreased skin radiance, or decreased skin tension.

In another aspect, described herein is a system for determining a maximum predicted skin quality of a human subject. The system comprises: at least one processor; at least one communications interface; and at least one tangible, non-transitory computer-readable storage medium having stored thereon a skin quality predictor, the skin quality predictor comprising computer executable instructions that, when executed by the at least one processor, cause the system to: (a) obtain an indication of a presence or absence of one or more polymorphisms of a set of human genes included in the human subject, wherein: (i) the presence or the absence of the one or more polymorphisms is determined from an analysis of nucleic acid from a biological sample from the human subject, (ii) the presence or absence of the one or more polymorphisms is associated with set of skin features, and (iii) the set of skin features are included in a set of skin features indicative of skin quality in humans and include at least two of skin wrinkles, skin spots, decreased skin tension, decreased skin radiance and skin texture roughness; (b) determine, for each polymorphism whose presence or absence was indicated in the obtained indication, a respective strength of correlation of the presence or absence of the each polymorphism to each skin feature included in the set of skin features; (c) determine, based on the respective strengths of correlation and based on a plurality of values corresponding to the set of skin features indicative of the skin quality of a plurality of other human subjects, wherein an age range of the plurality of human subjects spans at least five decades, a predicted skin quality value indicative of the maximum predicted skin quality of the human subject; and (d) cause the predicted skin quality value to be presented at a user interface.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. With respect to aspects of the invention described or claimed with "a" or "an," it should be understood that these terms mean "one or more" unless context unambiguously requires a more restricted meaning. The term "or" should be understood to encompass items in the alternative or together, unless context unambiguously requires otherwise. If aspects of the invention are described as "comprising" a feature, embodiments also are contemplated "consisting of" or "consisting essentially of" the feature.

BRIEF DESCRIPTION OF THE DRAWINGS

FIGS. 2A-2C illustrate an example scenario of an application of the method 100 to a particular human subject.

DETAILED DESCRIPTION OF THE INVENTION

Figure 1:
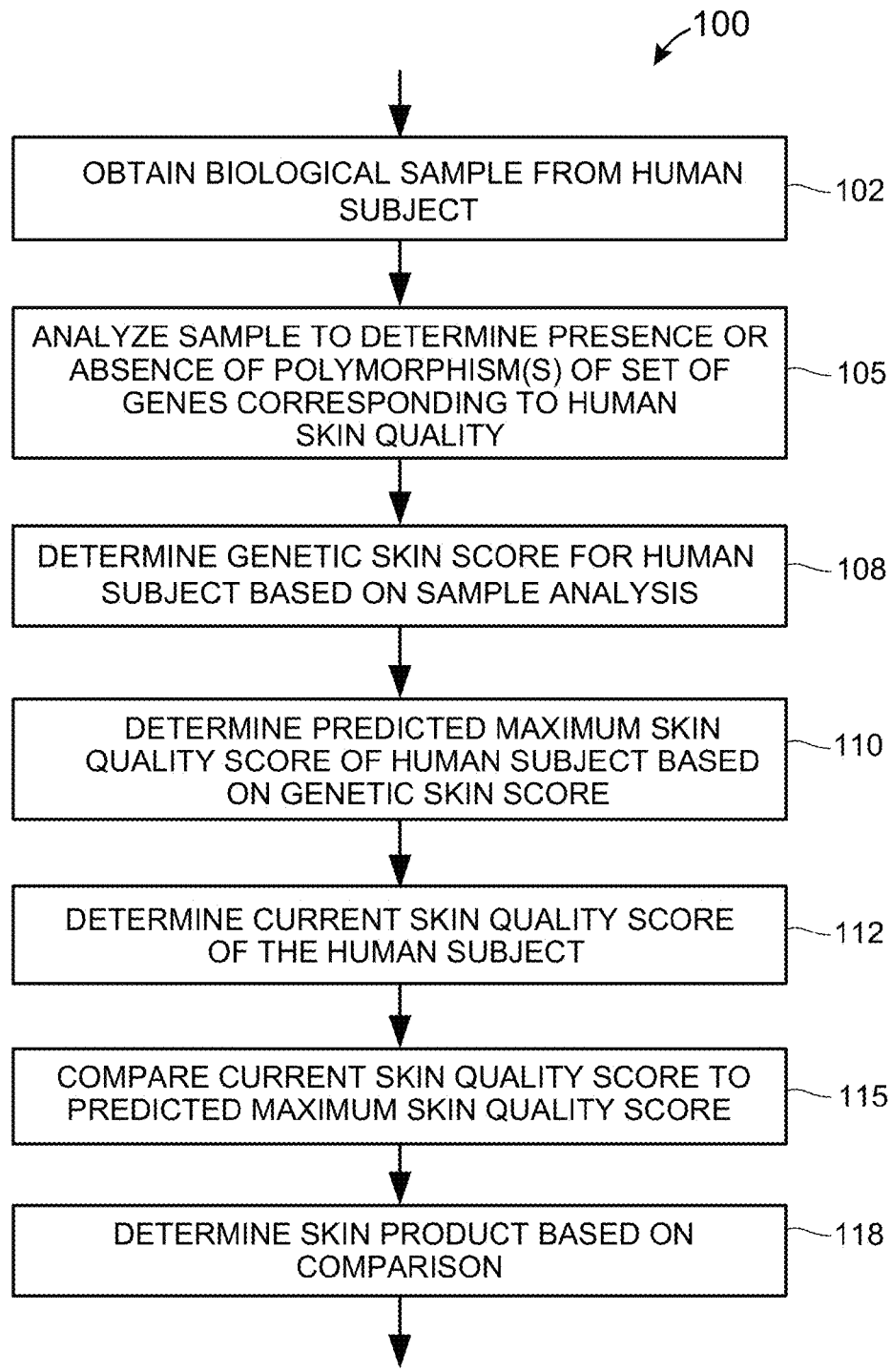
FIG. 1 illustrates an example method 100 of assessing the skin quality of a human subject.

A "polymorphism" is a sequence variation in a gene, DNA sequence, or chromosome, i.e., a position in the genome where more than one nucleotide sequence exists in a population. Generally, a "polymorphism" comprises a substitution or an insertion/deletion, although the term is not limited to such. A "single nucleotide polymorphism" ("SNP") is variation in a single base pair in a DNA or RNA sequence. Put another way, a SNP is an alternative form of a gene portion that varies from wild type (or another reference sequence) only in the identity of a single nucleotide residue in that portion. For example, without limitation, exchanging one A for one C, G or T in the entire sequence of polynucleotide constitutes a SNP. Of course, it is possible to have more than one SNP in a particular polynucleotide. Polymorphisms can also be larger in size. For example, polymorphisms include variations in multiple consecutive or closely-spaced, non-consecutive nucleotide residues.

The term "skin dimensions" (also referred to interchangeably herein as "skin conditions," "skin characteristics," "skin quality," or "skin features") as used herein refer to skin texture, skin tension, skin wrinkles, skin spots, or skin radiance.

The term "skin texture" generally refers to the topology or roughness of the skin surface.

The term "skin tension" or "skin firmness" generally refers to the firmness or elasticity of the skin.

The term "skin wrinkle" generally refers to a fold, ridge or crease in the skin, and includes fine lines, fine wrinkles and course wrinkles. Skin wrinkles are measured in terms of, for example, density and/or length.

The term "skin spots" generally refers to discoloration or uneven pigmentation (e.g., hyperpigmentation, blotchiness) of the skin. Skin spots are evaluated in terms of, e.g., density, size, and/or degree of discoloration.

The term "skin radiance" generally refers to an amount of light that the skin reflects.

The term "control subject" or "control human subject" refers to an actual or hypothetical human subject whose genome does not comprise a polymorphism of interest, such as a polymorphism of interest assessed by the methods disclosed herein.

The term "control group" refers to subjects in a group population that has not used a specific skin product before being tested. Members of the control group may or may not have polymorphisms in any of the assessed genes.

The term "reference SNP" or "rs" refers to a reported polymorphic variation, including summary information for the variation and a summary of allele frequencies as maintained by the National Center for Biotechnology Information (NCBI).

The term "current skin quality score(s)" refers to a quantitative indication of the quality or severity of a respective skin feature in a human subject at the time of evaluation. For example, when a current skin quality score is prepared via image analysis, the score is calculated at the time the image(s) were captured or shortly thereafter (e.g., 30 days or less after the image(s) are captured).

The term "genetic skin score" refers to respective correlation of the presence or absence of each polymorphism to the skin feature.

The term "predicted skin feature quality score" refers to a quantitative indication of the quality or severity of a respective skin feature in a human subject, such as a quantitative indication of the quality or severity of a respective skin feature at a later time after the evaluation. For example, when a predicted skin quality score is obtained via DNA analysis, the score is calculated by applying a predictive equation to a genetic skin score Other terms associated with the disclosure are defined below.

Methods of Assessing Skin Quality

In one aspect, the invention is predicated, at least in part, on the discovery of a relationship between a subject's particular nucleotide (allele) or genotype at the site of given polymorphisms in skin-related genes (e.g., SOD2, MMP1 and GPX1) and multiple skin features (e.g., skin wrinkles, skin spots, skin texture, skin radiance, and skin tension). In particular, the applicants discovered that the prevalence of single nucleotide polymorphisms (SNPs) in the skin-related genes allows for prediction of a subject's susceptibility of developing imperfections in those multiple skin features.

The complex etiologies associated with skin imperfections are influenced by a combination of genetic and environmental factors unique to each condition. Indeed, skin imperfections are caused by any of a number of physiological, behavioral, and environmental dynamics, such as, for example, the natural aging process, illness, diet, allergens, hormonal changes, sun exposure, alcohol use, lack of sleep, and tobacco use. Given the broad spectrum of underlying causes of skin imperfections, the identification of genetic markers predictive for multiple skin features was unpredictable. The discovery of a strong correlation between polymorphisms in SOD2, MMP1 and GPX1 and multiple skin imperfections allows evaluation of a human subject's skin health potential, which has not been achieved previously. Therefore, the invention represents an advancement in the art. Additionally, the correlation between SOD2, MMP1 and GPX1 polymorphisms and undesirable skin features was observed to increase with age, i.e., the relationship between the polymorphisms and the measured features was stronger in subjects aged 40 and above. Therefore, the invention might most benefit those subjects aged 40 and above.

In another aspect, by combining DNA analysis with visual or image analysis, current skin quality and predicted skin quality of a human subject can be ascertained, allowing for a comprehensive analysis of a subject's skin health and potential. This is particularly useful information as the subject ages, preferably for those subjects aged 40 and above. With this knowledge in hand, a subject can be counseled to select a skin care regimen that not only addresses current skin concerns relating to, e.g., skin wrinkles, skin spots, skin firmness, skin brightness and skin tension, but also addresses future risk of developing one or more of these undesirable skin features. As such, in one aspect, the disclosure provides a system and method for providing customized, "concierge" counseling to skin care product consumers.

In one aspect, the invention includes a method of assessing the skin quality of a human subject. The method comprises determining the presence or absence of polymorphisms in MMP1, SOD2, and GPX1 in a biological sample from the human subject to provide a genetic skin score for the human subject; and determining a predicted skin feature quality score corresponding to a skin feature. The skin feature is selected from the group consisting of skin wrinkles, skin spots, decreased skin tension, decreased skin radiance, and skin texture roughness. The predicted skin feature quality score is determined by applying a predictive equation corresponding to the skin feature to the genetic skin score. The predictive equation is determined by a regression analysis of data obtained from a control group comprising human members whose ages span at least five decades. The data comprises (i) a genetic skin score of each member of the control group, and (ii) a plurality of measurements corresponding to each member of the control group and associated with the skin feature. The plurality of measurements are calculated from an image analysis of a skin surface of each member of the control group. In various embodiments, the predicted skin feature quality score is representative of a risk of the human subject developing the skin feature.

Optionally, the method described herein comprises determining a respective predicted skin feature score for two, three, four, or all five skin features selected from the group consisting of skin wrinkles, skin spots, decreased skin tension, decreased skin radiance, and skin texture roughness. Thus, in some embodiments, the genetic skin score is applied in five different predictive equations to calculate predicted skin feature scores for each of skin wrinkles, skin spots, decreased skin tension, decreased skin radiance, and skin texture roughness. Thus, in one aspect, the method of the invention provides information regarding a subject's relative risk of developing five different skin features, which allows a more comprehensive evaluation of consumer needs for skin care.

Additionally, the invention provides a method of assessing the skin quality of a human subject wherein the method comprises determining the presence or absence of polymorphisms in skin-related genes, such as for example, MMP1, SOD2, and GPX1 in a biological sample from the human subject to provide a genetic skin score; and determining a respective skin feature quality score for each of a group of skin features comprising skin wrinkles, skin spots, decreased skin tension, decreased skin radiance, and skin texture roughness. Each respective skin feature quality score is calculated by applying a respective predictive equation to the genetic skin score. Put another way, a unique predictive equation for each of skin wrinkles, skin spots, decreased skin tension, decreased skin radiance, and skin texture roughness is applied to the genetic skin score, resulting in five predictive skin feature quality score scores, each of which corresponding to a different skin feature. The predictive equations are based on the respective strengths of correlation of the presence or absence of polymorphisms in MMP1, SOD2, and GPX1 to the respective skin feature.

Optionally, each respective predictive equation is based on a normalization of the respective strengths of correlation of the presence or absence of polymorphisms in MMP1, SOD2, and GPX1 to each of the skin features. In various aspects, an indication of each of the respective strengths of correlation of the presence or absence of a polymorphism in MMP1, SOD2, and GPX1 to each of the skin features is applied to a different portion of the genetic score. In various aspects, the predicted skin feature quality scores are representative of a risk of the human subject developing each of the skin features.

In various embodiments, the method includes an evaluation of the observable quality of the subject's skin condition. Thus, the invention allows a comparison of the subject's skin "potential" (i.e., the likelihood of developing low or high risk of skin imperfections) and the subject's current skin condition. In this regard, the methods described herein optionally comprise determining a current skin feature quality score of the human subject from image analysis, i.e., analysis of an image of a skin surface of the human subject. The current skin feature quality score corresponds to the same skin feature for which the predictive skin feature quality score is generated. The method then comprises determining a magnitude of a gap between the (i) predicted skin feature quality score and (ii) the current skin feature quality score.

In this regard, it is understood that the larger the magnitude of the gap, the worse off the subject's skin condition is relative to the genetic potential. For these subjects, it is vital that they are aware of this information in order to ensure suitable skin care products are recommended/chosen to help minimize the magnitude of the gap. It is desirable that this information is obtained earlier in the subject's life (e.g., 40 years or below, 35 years or below, 30 years or below, or 25 years or below), so as to increase any benefits derived from use of the skin care products.

In another regard, while the smaller the magnitude of the gap reflects the subject's better "nurturing" of their skin up to that point in time, there is no assurance that the magnitude of the gap will continue to remain small as the subject ages. This is due in part to the changing physiology of the body with age. As noted above, the correlation between the presence and absence of the SNPs and the respective skin features increases with age. For example (and not wishing to be bound by any particular theory), a subject with a SNP in MMP1 produces collagenase, an enzyme known to breakdown collagen in the body, at an increased rate as compared to a control subject. Moreover, collagenase production generally increases with age. Collagen is a long, fibrous structural protein that gives skin its strength and elasticity. Collagen degradation is the major contributor to skin wrinkling and loss of suppleness and elasticity. Therefore, the combination of SNP in MMP1 and aging will result in more collagen breakdown and skin aging as compared to control subjects that do not possess the SNP. As the subject with the SNP in MMP1 ages, her skin care needs will change, requiring possibly different skin products to ones to which she is currently using, e.g., contains more collagen to supplement the body's naturally occurring age-related decrease of collagen in the body. Therefore, this invention also would benefit those subjects who magnitude of the gap is small.

Where two, three, four, or all five skin features are evaluated, the methods described herein optionally comprise determining, based on image analysis of an image of a skin surface of the human subject, a respective current skin feature quality score corresponding to each skin feature evaluated. A respective magnitude of a respective gap between the predicted skin feature quality score and the current skin feature quality score is determined for each skin feature. If desired, the skin feature associated with the largest gap magnitude is identified. For example, the method allows identifying skin features having current skin feature scores indicating a greater severity in skin condition (i.e., worse skin condition) than would be predicted by the predicted skin feature score, and prioritizing the skin features with the greatest discrepancies in scores to, e.g., help to select or recommend a skin care regimen for the subject. Indeed, the method optionally comprises identifying a skin product suitable for improving the appearance of the skin feature(s).

The methods described herein optionally comprise counseling the human subject with respect to a skin product suitable for improving the appearance of the particular skin feature, wherein the skin product selected is based on the magnitude of the gap between the current skin feature quality score and the predicted skin feature quality score.

Figure 2C:
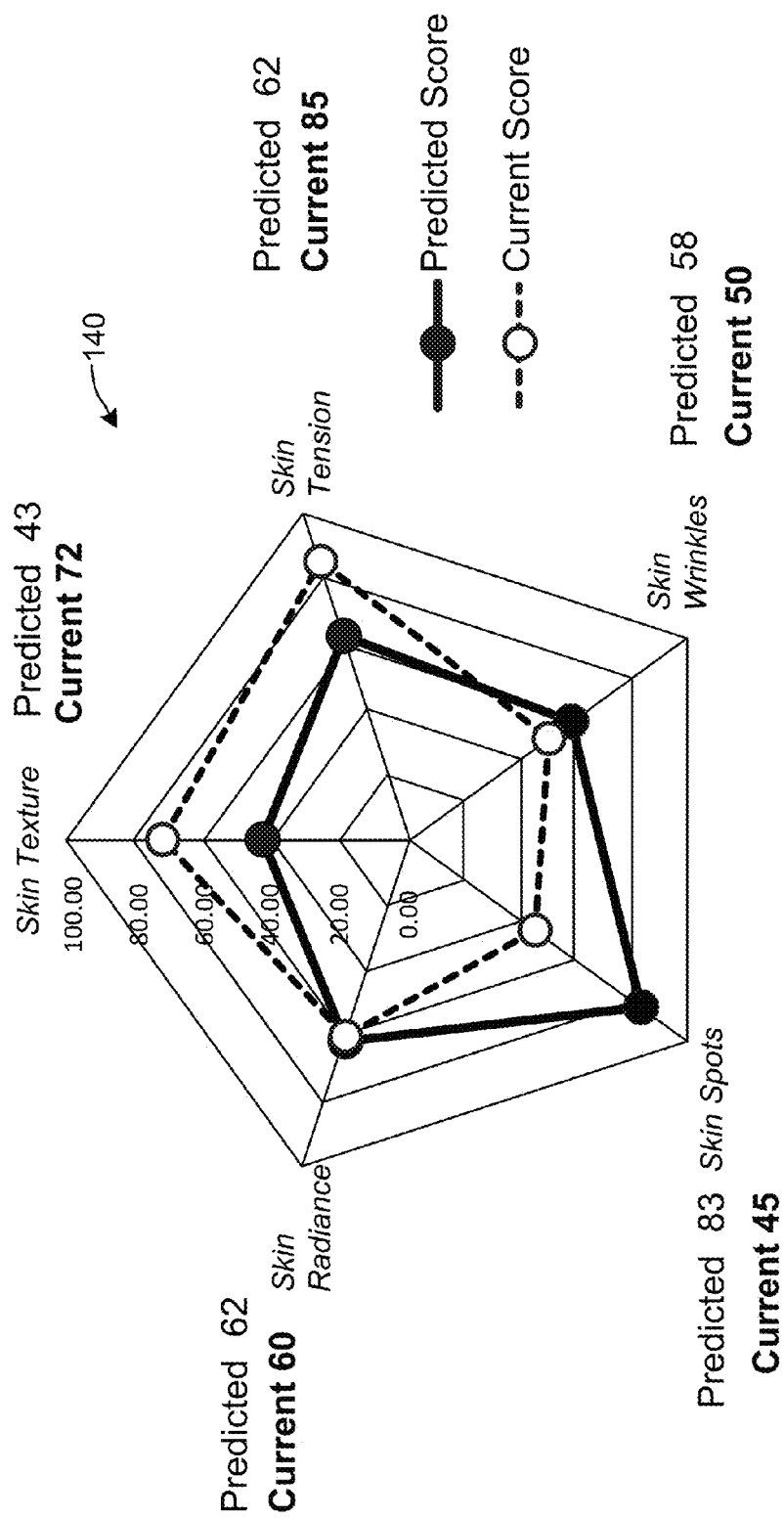
Figure 3:
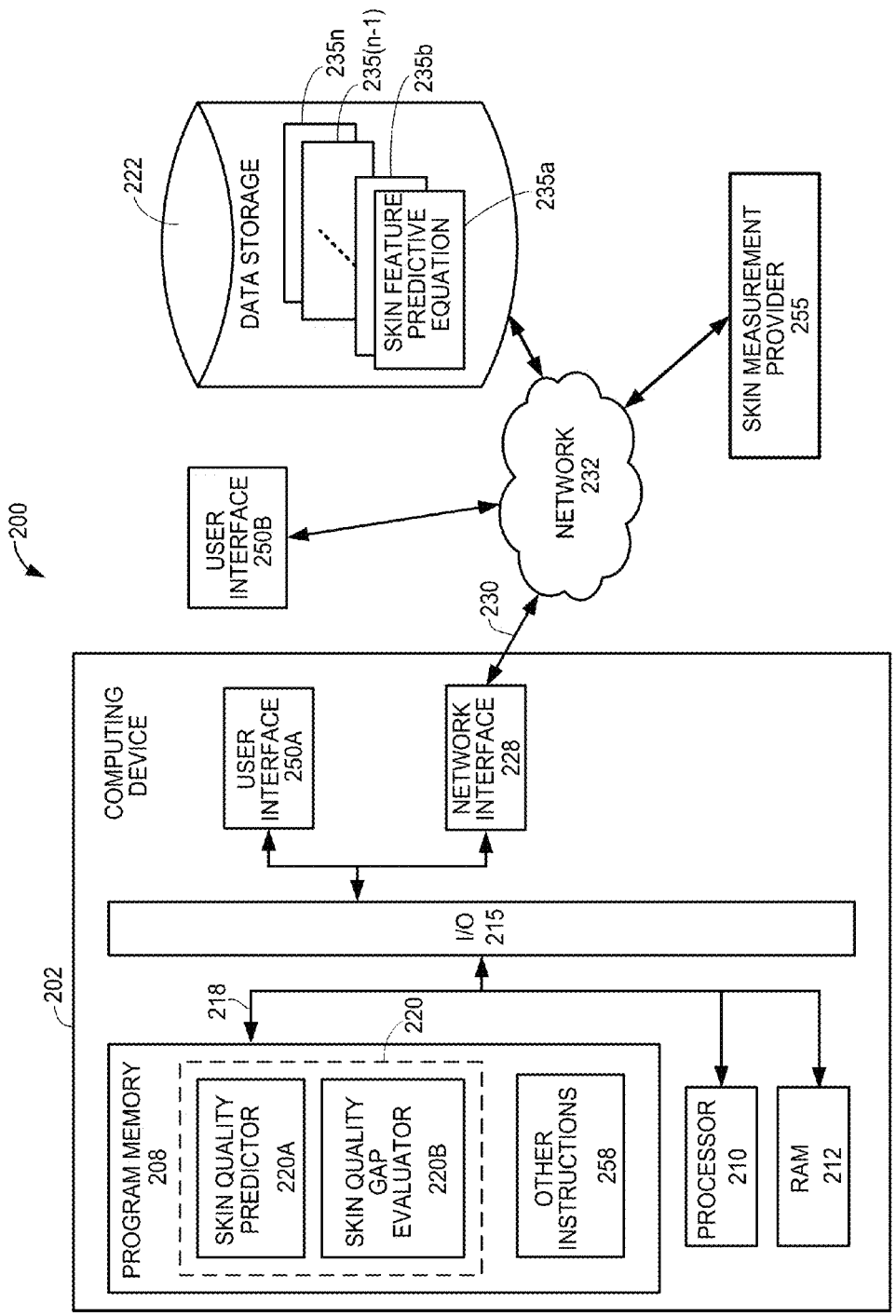
FIG. 3 illustrates an embodiment of a system 200 for assessing the skin quality of a human subject.

Methods of assessing skin quality of a human subject can also be described as shown in FIGS. 1-3. FIG. 1 illustrates an example method 100 of assessing the skin quality of a human subject, such as a consumer of cosmetic or skin care products. Not all steps illustrated in FIG. 1 are required in the context of the invention, but are provided to illustrate various aspects of the invention.

The method 100 comprises obtaining a biological sample from the human subject (block 102). The biological sample may be obtained 102 from any source of the human subject which contains genomic DNA, such as, for example, saliva, blood, amniotic fluid, cerebrospinal fluid, or virtually any tissue sample (e.g., from skin, hair, muscle, buccal or conjunctival mucosa, placenta, gastrointestinal tract or other organs). The biological sample is obtained from a subject using any clinically-accepted method. In some embodiments, the biological sample is obtained non-invasively via, e.g., swabbing or scraping the inside of the mouth. The swab (e.g., a handle attached to one or two fibrous heads made of, for example, cotton or dacron) or plastic scraper is optionally allowed to dry prior to packaging for analysis. The biological sample also may be obtained by use of adhesive tape to obtain skin surface cells for analysis. Optionally, the biological sample can be self-collected in the home of the subject using a kit comprising materials for DNA sample collection. An exemplary kit is described in, for example, U.S. Pat. No. 6,291,171, which is hereby incorporated by reference. The collected sample may thereafter be sent directly to the laboratory for analysis.

At block 105, the biological sample is analyzed to determine the presence or absence of one or more polymorphisms of one or more skin-related genes associated with one or more "skin dimensions" (also referred to interchangeably herein as "skin conditions," "skin characteristics," or "skin features") that correspond to or impact the quality or condition of human skin features. Skin features include, but are not limited to, skin texture, skin tension, skin wrinkles, skin spots, and skin radiance. Although five skin dimensions are discussed herein, these five skin dimensions are exemplary only, and the presence or absence of one or more polymorphisms of genes associated with other skin features may also be utilized with respect to the methods, systems and techniques described herein.

Referring still to block 105, the biological sample from the human subject may be analyzed to determine the presence or absence of a polymorphism (i.e., one or more polymorphisms) of one or more genes that affect skin features. In one aspect, the method preferably comprises detecting a polymorphism in the following three genes MMP1, SOD2, and GPX1 (although the method also may be performed by detecting only one or two of the identified genes). MMP1 (Matrix Metalloproteinase 1, also known as collagenase 1) was observed to be correlated with at least two skin features, e.g., skin wrinkles and skin texture. The polymorphism in MMP1 is optionally an insertion (e.g., insertion of guanine) at position 3471 of the nucleic acid sequence of GenBank Accession No. NG 011740.1. (Reference SNP(refSNP) Cluster Report: rs1799750; http://www.ncbi.nlm.nih.gov/projects/SNP/snp_ref.cgi?rs=1799750)

SOD2 (Superoxide dismutase 2) was observed to be correlated with at least two skin features, e.g., skin tension and skin texture. In various embodiments, the polymorphism in SOD2 is a substitution (e.g., a cytosine to thymine substitution) in position 5482 of the nucleic acid sequence of GenBank Accession No. NG 008729.1, which results in a substitution of alanine for valine at amino acid position 16 in the resulting SOD2 peptide. (Reference SNP(refSNP) Cluster Report for rs4880; http://www.ncbi.nlm.nih.gov/projects/SNP/snp_ref.cgi?rs=4880)

GPX1 (Glutathione Peroxidase 1) was observed to be correlated with at least two skin features, e.g., skin spots and skin tension. The polymorphism in the GPX1 gene is optionally a missense mutation at position 5958 of the nucleic acid sequence of GenBank Accession No. NG 012264.1 wherein cytosine is substituted with thymine, resulting in a substitution of proline with leucine at amino acid position 200 in the GPX1 peptide. (Reference SNP (refSNP) Cluster Report: rs1050450; http://www.ncbi.nlm.nih.gov/projects/SNP/snp_ref.cgi?rs=1050450)

Optionally, the polymorphisms in the three genes correspond to their respective SNP IDs: rs1799750 (MMP1), rs4880 (SOD2), and rs1050450 (GPX1). Other genes with polymorphisms which have been shown to affect one or more skin dimensions are provided in Table 1. Optionally, these other skin-related genes are substituted for any of the three genes mentioned above or can be included in addition to the three genes mentioned above in the methods described herein.

TABLE 1

SNPs for Other Skin-Related Genes and Impact on Skin Features

| SNP | Polymorphisms | Impact on Skin Features/Wellness |
| --- | --- | --- |
| mEPHX (Microsomal epoxide hydrolase) rs 1051740 | Y113H | Subjects having this SNP tend to have higher number of pores in the nose and cheek regions. |
| TNFα (Tumor necrosis factor alpha) rs 1800629 | A-308G | Subjects having SNPs at the 308th site (G/A type or AA type) have a relatively thin epidermal layer. |
| HAS3 (Hyaluronan Synthase 3) 234 known SNPs | Various | Subjects with SNPs in this gene have reduced production of hyaluronic acid in the epidermis and the corium, which is a major constituent of the extra cellular matrix (ECM). |

TABLE 1-continued

SNPs for Other Skin-Related Genes and Impact on Skin Features

| SNP | Polymorphisms | Impact on Skin Features/Wellness |
| --- | --- | --- |
| COLIA1 (Collagen Type 1 Alpha) | Various | Subjects with SNPs in this gene have reduced production of collagen in the epidermis and corium. |
| PPARδ (Peroxisome proliferator-activated receptor delta) | Various | Subjects with SNPs in this gene have reduced skin homeostasis functionality. |
| AQP3 (Aquaporin 3) | Various | Subjects with SNPs in this gene have reduced formation of water channels in the epidermis and corium. |
| MC1R (Melanocortin-1-receptor) | Various | Caucasian subjects having this SNP have enhanced freckles. |
| PON1 (Paraoxonase 1) rs662 | R192Q | Subjects with SNPs in this gene have variable PON1 levels in circulation, which may result in higher oxidized levels of LDL and diminished cardiovascular health |
| MTHFR (Methylene Tetrahydrofolate Reductase) rs1801133 | C667T | Subjects with SNPs in this gene have increased levels of homocysteine. |
| MTRR (Methionine Synthase Reductase) rs1801394 | A66G, Ile22Met | Subjects with SNPs in this gene have reduced ability to clear homocysteine. |
| VDR (Vitamin D Receptor) rs10735810 | T2M | Subjects with SNPs in this gene may have reduced bone mineral density and abnormal cell division. |
| NQO1 (Coenzyme Q10 Reductase) rs1800566 | P187S | Subjects with SNPs in this gene have reduced antioxidant levels. |
| CYP11B2 (Aldosterone Synthase) rs1799998 | C-344T | Subjects with SNPs in this gene have diminished cardiovascular health. |
| ApoB rs693 | C2514T | Subjects with SNPs in this gene have increased cholesterol and impaired glucose tolerance. |

The presence or absence of polymorphisms is determined using any suitable method. The method by which detection of polymorphisms is not critical. For example, occurrence of the polymorphisms can be detected by a method including, but not limited to, hybridization, restriction fragment length analysis, invader assay, gene chip hybridization assays, oligonucleotide ligation assay, ligation rolling circle amplification, 5' nuclease assay, polymerase proofreading methods, allele specific PCR, matrix assisted laser desorption ionization time of flight (MALDI-TOF) mass spectroscopy, ligase chain reaction assay, enzyme-amplified electronic transduction, single base pair extension assay, reducing sequence data and sequence analysis.

The polynucleotide material used in the analysis can be DNA (including, e.g., cDNA) or RNA (including, e.g., mRNA), as appropriate. Optionally, the RNA or DNA is amplified by polymerase chain reaction (PCR) prior to hybridization or sequence analysis. For hybridization, the polynucleotide sample exposed to oligonucleotides specific for region of the sequence associated with the polymorphism, optionally immobilized on a substrate (e.g., an array or microarray). Selection of one or more suitable probes specific for an locus of interest, and selection of hybridization or PCR conditions, are within the ordinary skill of scientists who work with nucleic acids.

The results of the genetic analysis are used to determine a genetic skin score for the human subject (block 108). In some embodiments, the genetic skin score is represented as a combination of respective weightings corresponding to the presence or absence of each polymorphism (e.g., the polymorphisms of MMP1, SOD2 and GPX1) on one or both alleles. For example, a wildtype genotype (i.e., absence of the polymorphism) may be weighted less than a heterozygous genotype (i.e., the polymorphism being present on one allele), which in turn may be weighted less than a homozygous genotype (i.e., the polymorphism being present on both alleles). The "genetic skin score" includes the weighted values corresponding to the polymorphism status of each gene tested.

As an illustrative but non-limiting example of the blocks 105 and 108, a buccal mucosal sample obtained from the human subject is analyzed to determine the presence or absence of polymorphisms in the three genes MMP1, SOD2, and GPX1. Each polymorphism's presence or absence in its respective gene (i.e., status) is reflected by a respective weighting (e.g., wild genotype=1, heterozygous genotype=2, homozygous genotype=3). The genetic skin score includes the weightings corresponding to each polymorphism's presence or absence in the biological sample of the human subject (e.g., MMP1=3, SOD2=2, GPX1=2).

At block 110, a predicted skin feature quality score is determined based on the genetic skin score of the human subject. For example, the genetic skin score of the human subject may be inputted into or operated on by a predictive equation to determine the predicted skin feature quality score of the human subject, or the predicted equation may be applied to genetic skin score. In some aspects, the predictive equation (described in more detail below) is based on the respective strengths of correlation of the presence or absence of the polymorphisms to the respective skin feature. Optionally the predictive equation is based on a normalization of the respective strengths of correlation of the presence or absence of polymorphisms in the tested skin-related genes (e.g., MMP1, SOD2, and GPX1).

Figure 5:
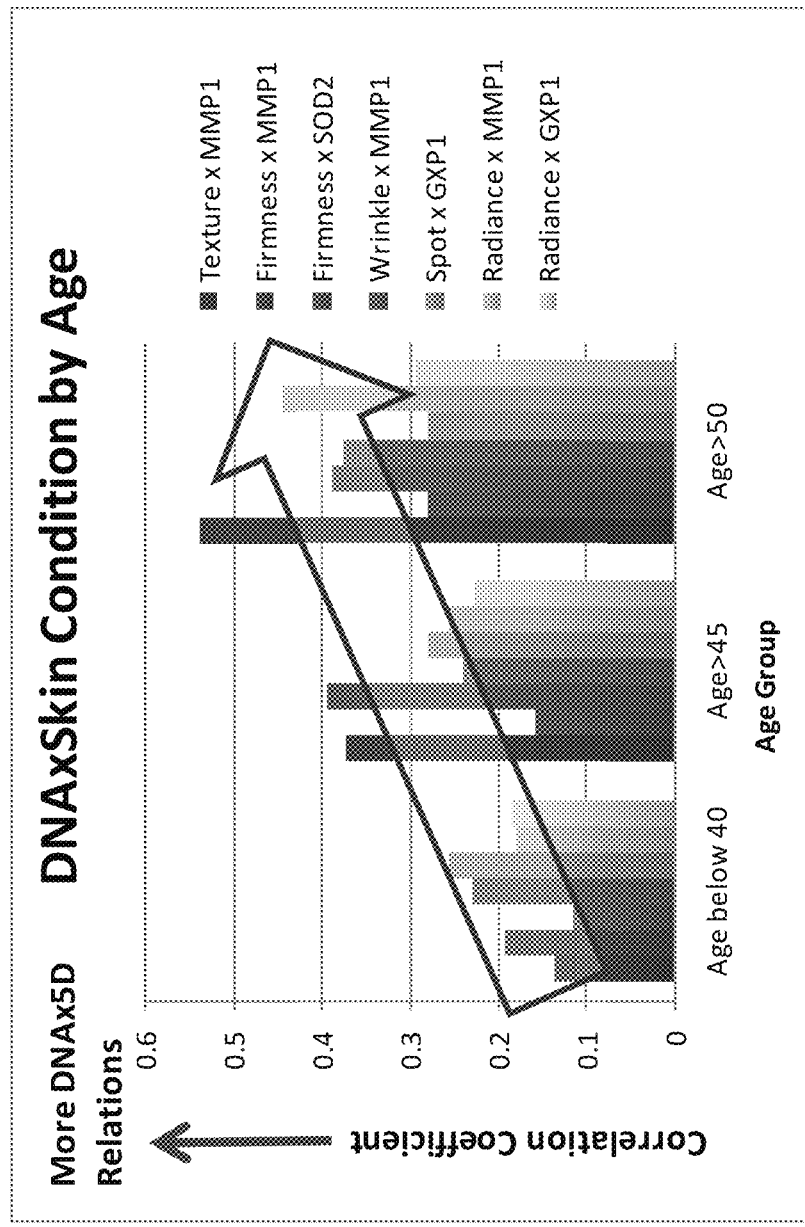
FIG. 5 is a bar graph illustrating the relationship between correlation coefficients for polymorphisms in MMP1, SOD2, and GPX1 with respect to skin texture, skin firmness (tension), skin wrinkles, skin spots, and skin radiance (y-axis) and age (x-axis). The correlations increase with age of the subject.
Figure 6A:
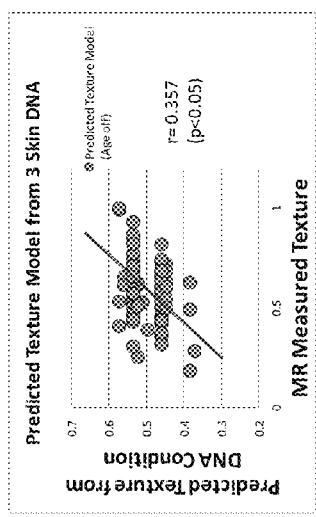
FIG. 6A-6E are line graphs correlating predictive skin quality scores prepared from a control group (y-axis) with current skin feature quality scores (x-axis) obtained from the same group of subjects for skin texture/roughness (FIG. 6A), skin wrinkles (FIG. 6B), skin radiance (FIG. 6C), skin firmness (FIG. 6D), and skin spots (FIG. 6E). The predictive skin quality scores were calculated using genetic skin scores representative of the presence or absence of single nucleotide polymorphisms in MMP1, SOD2, and GPX1 (i.e., wild-type, heterozygous polymorphism, or homozygous polymorphism). The models demonstrate a significant relationship between the predicted skin feature quality score and actual skin measurements obtained by image analysis.
Figure 6B:
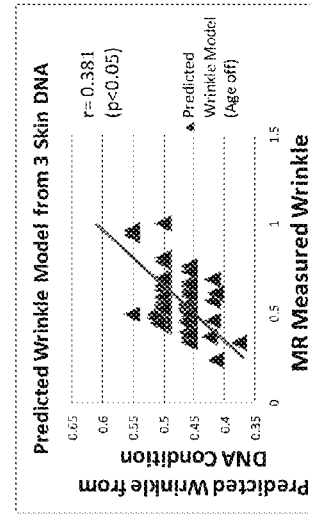
Figure 6C:
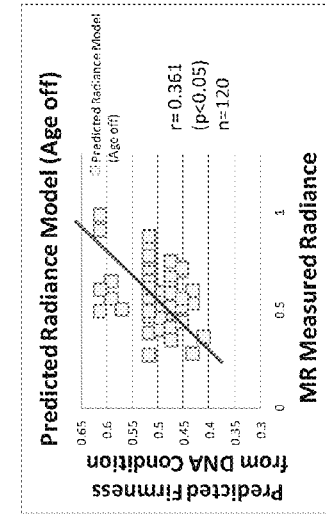
Figure 6D:
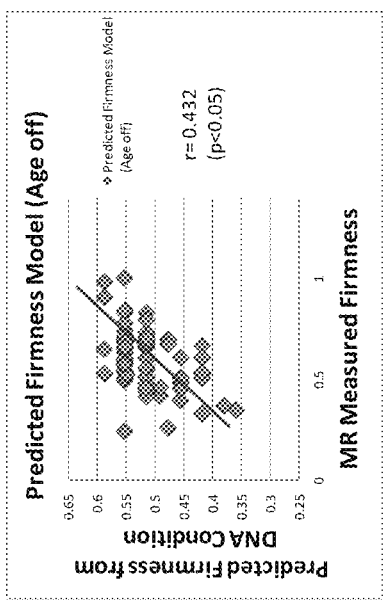
Figure 6E:
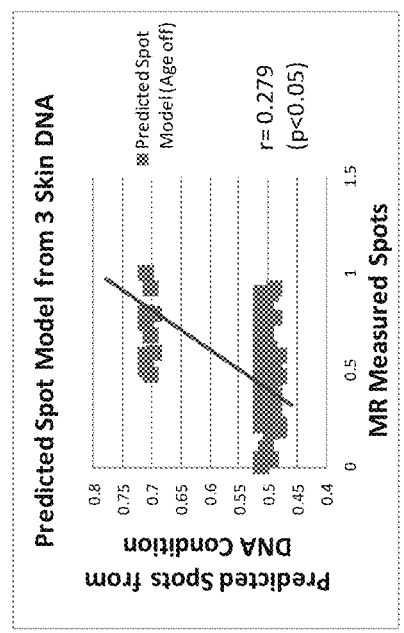

In some embodiments, the predicted skin feature quality score of the human subject corresponds to the risk of developing one or more skin features (e.g., decreased skin radiance, decreased skin tension, increased skin roughness, skin wrinkles, or skin spots) over the lifetime of the subject (or at least over an extended period of time, such as, for example, at least a decade, at least two decades, at least four decades or at least five decades). Therefore, it is an effective system and method to generate information for evaluation or assessment of future skin quality. Indeed, as illustrated in FIG. 5, the correlation between polymorphisms in MMP1, SOD2, and GPX1 and the skin dimensions tested is stronger in aged subjects. In various aspects, the predicted skin quality score is representative, or a quantitative indication, of a subject's skin quality (at least with respect to the skin feature analyzed) over an extended period of time, such as, for example, subjects aged 40 and above. A predicted skin quality score also can be considered as a measure of skin "potential," and, as such, provides useful information in counseling a consumer on possible improvements in skin features or development of skin imperfections. Further, a predicted skin quality score also can be used to personalize skin care systems and methods of recommendation to a consumer based, in part, on information gathered about the consumer's genes.

In an embodiment, a predicted skin feature quality score is determined for each skin dimension or skin feature (e.g., skin wrinkles, skin spots, skin texture, skin tension, and skin radiance, or any combination thereof). For example, a method of calculating a predicted skin feature quality score is to take a population with subjects having ages that span several decades and analyze each of them for the presence of absence of SNPs in the three genes (MMP1, SOD2 and GPX1). With that data, it is possible to then formulate a "predictive equation" for each skin feature (i.e., a "respective predictive equation") which correlates to the prevalence of those SNPs to the skin features, and applied to the genetic skin score.

These feature-specific predicted skin feature quality scores are referred to herein as "respective predicted skin feature quality scores," and each predicted skin feature quality score may be representative or indicative of a risk of developing the respective skin feature over an extended period of time, or may be representative or indicative of a maximum degree of development of the respective skin feature in the human subject (e.g., development over an extended period of time). For example, a first predictive equation may operate on the genetic skin score to determine a predicted increased skin texture roughness quality score, a second predictive equation may operate on the genetic skin score to determine a predicted skin spots score, and a third predictive equation may operate on the genetic skin score to determine a predicted decreased skin tension score.

In one aspect of the invention, the predictive equation is determined based on a population of human subjects (a "control group") having an age range of at least for decades, preferably a decade, at least two decades, at least three decades, at least four decades, or at least five decades (e.g., ages ranging from the mid-twenties to the mid-seventies). Each respective predictive equation optionally includes a factor corresponding to a correlation of a particular SNP to the development of the respective skin feature. In an embodiment, the value of each factor may be determined by a regression analysis of genetic and skin feature data corresponding to a population of subjects, such as described herein. In some embodiments, multiple SNPs are accounted for in the predictive equations and accordingly, each respective predictive equation may include a respective factor for each SNP's correlation to the development of the respective skin feature over an extended period of time. For example, each predictive equation may follow the format:

$$\text{predicted\_skin\_feature\_quality\_score} = \\ (\text{Factor}_{gene\_1} * \text{genetic\_skin\_score}_{gene\_1}) + \\ (\text{Factor}_{gene\_2} * \text{genetic\_skin\_score}_{gene\_2}) + \ldots + \\ (\text{Factor}_{gene\_n} * \text{genetic\_skin\_score}_{gene\_n})$$

The factors associated with different SNPs generally differ (e.g., Factor$_{gene\_1}$ typically differs from Factor$_{gene\_2}$). Of course, other formats of predictive equations may be possible and may be utilized to generate a predicted skin feature quality score. For example, more than one skin feature may be reflected in a single predictive equation, or the weights corresponding to multiple genes may be combined in ways other than or in addition to summing Example 1 describes one of many possible methods of preparing predictive equations. As discussed in Example 1, biological samples were obtained from 235 human subjects ranging in age from 28 years to 76 years. Each biological sample was analyzed to determine a respective genetic skin score corresponding to MMP1, SOD2, and GPX1, e.g., by using techniques similar to those discussed with respect to block 105. Additionally, images of one or more portions of the skin surface of each person in the population were captured, and these images were automatically analyzed to determine calculated measurements of respective skin features (i.e., respective skin texture, respective skin tension, respective skin spots, respective skin wrinkles, and respective skin radiance) of each human subject.

A regression analysis was performed on the genetic skin scores and the measured skin features of the population, and predictive equations corresponding to the various skin features were determined from the regression analysis. Regression analysis is well understood in the art. Regression analysis with a single explanatory variable is termed "simple regression," while "multiple regression" techniques consider additional parameters separately so that the effect of each parameter can be estimated. Regression techniques include, e.g., linear regression, ordinary least squares regression, multiple regression, nonlinear regression, nonparametric regression, Bayesian methods, logistic regression, regression models with more predictor variables than observations, and causal inference with regression. Any of these regression techniques, either alone or in combination, may be used to determine one or more portions of the predictive equation(s).

The predictive equations corresponding to the various skin dimensions were determined to be:

Predicted Skin Texture Roughness Increase Score=
(0.0374480639969673×weight_$GPX$1+
0.0757841036753773×weight_$MMP$1+
0.0127142963552415×weight_$SOD$2+
0.233626653284045)  (equation 1);

Predicted Skin Tension Decrease Score=
(0.0351630451918284×weight_$GPX$1+
0.0374418222614438×weight_$MMP$1+
0.0965339564177257×weight_$SOD$2+
0.115478641551425)  (equation 2);

Predicted Skin Wrinkles Score=
(0.0507559183830409×weight_$GPX$1+
0.0431677157685105×weight_$MMP$1+
0.0379291897697488×weight_$SOD$2+
0.207374358966336)  (equation 3);

Predicted Skin Spots Score=(0.198211763414803×weight_$GPX$1+0.0083324394521924×weight_$MMP$1+0.01462674646227×weight_$SOD$2+
0.246233861182508)  (equation 4);

and Predicted Skin Radiance Decrease Score=
(0.0954719152649371×weight_$GPX$1+
0.0424280862986934×weight_$MMP$1+
0.0217567441950868×weight_$SOD$2+
0.229078291144297)  (equation 5), where the syntax "weight_<gene>" indicates an aggregated or combined weight of the genotypes corresponding to the polymorphism(s) of <gene>. In the context of the illustration above, which is provided merely to illustrate the invention and is not to be construed to be limiting, "weight_<gene>" is 1 for wild-type genotype (associated with low risk), 2 for heterozygous polymorphisms (associated with medium risk), and 3 for homozygous polymorphisms (associated with high risk).

Of course, one skilled in the art will recognize that embodiments other than those used in Example 1 may be utilized to prepare predictive equations and/or to increase the accuracy of the predictions of the predictive equations. For example, the sample population size whose data the regression analysis is performed upon may be increased, or the maximum age of the population size may be increased (or decreased). Additionally or alternatively, the specificity, accuracy, or number of the measurements or calculations of the image analyses may be increased. The coefficients in equations 1-5 may fluctuate by, e.g., 1%, 5%, 10%, 15%, 20%, or 25% (or range from about 0.001 to about 0.10 or any subrange therein, e.g., from about 0.01 to about 0.08 or about 0.02 to about 0.04).

As the predictive equation(s) are, in various aspects, determined from a population of subjects across an expected lifetime (or across an extended duration of time of desired skin quality), the predicted skin feature quality score of the human subject may be normalized with respect to the population. In one aspect, the odds ratio ("OR," e.g., OR=1.3) is used to represent the correlation between the genetic linkage (polymorphism) and one or more skin conditions (and/or the weight of the correlation). Image analysis also is optionally considered in the predictive equation(s), and the numerical (e.g., percentage) output of the predictive equation(s) is then optionally based on a combination of the odds ratio (genetic component) and a current image analysis. The output of the predictive equation(s) may be converted into a scoring system. For example, a predicted skin wrinkles quality score of 72 for the human subject may indicate that, over a period of time, preferably over an extended period of time, the human subject may have a 72% risk of developing wrinkles as compared with the population. In another example, a predicted skin wrinkles quality score of 65 may indicate that the human subject is predicted to have a maximum of 15% more wrinkles than an average maximum amount of wrinkles of the population when, e.g., a score of 50 represents an average maximum amount of wrinkles for the population.

In an embodiment, in addition to the genetic skin score of the human subject, the predictive equation(s) may also receive an age (e.g., a future age) as an input. For example, if the genetic skin score and a future age (e.g., 55 years) is entered into a predictive equation corresponding to skin spots, the resulting predicted skin spots quality score may indicate a predicted maximum of skin spots (as compared with the population) when the human subject reaches the age of 55 years.

Returning to the method 100, the method 100 may include determining a current skin feature quality score of the human subject (block 112). In an embodiment, the current skin feature quality score is determined by automatically analyzing an image of one or more portions of the skin surface of the human subject. The image analysis, in some embodiments, is configured to determine the plurality of measurements associated with the group of skin features based on at least one of: a line on the skin surface, the line determined based on a shadow in the image; a brightness of an area of the shadow; a length and a width of the line; a horizontal-to-vertical ratio of the line; a linearity of the line; a circularity of the line; a total area of the line; a mean direction of the line; a quantity of lines detected on the skin surface; a depth of spectrum constitution of one or more portions of the image; a size of the one or more portions having a particular depth of spectrum constitution; a size of an image of one or more sebaceous glands captured in the image of the skin surface; or an angle of the one or more sebaceous glands captured in the image of the skin surface.

Example 1 describes one of many embodiments of determining a current skin quality score (block 112). In this embodiment, a Magic Ring® brand skin analysis system (as described in Miyamoto, K. et al., Skin Res. Tech., 19:e525-e531, 2013, the entire disclosure of which is incorporated herein by reference) captures one or more images of one or more sections of the skin surface of the human subject, e.g., the cheek and nasolabial cheek regions. The Magic Ring® brand skin analysis system performs an analysis of the images, and calculates or infers, based on the image analysis, quantitative measurements corresponding to a set of skin dimensions or features. For example, the Magic Ring® brand skin analysis system filters one or more shadows of the captured images to determine the presence of wrinkles on the skin surface, and/or the Magic Ring® brand skin analysis system measures the filtered shadows to calculate the density, length, and direction of the wrinkles. Additionally or alternatively, the Magic Ring® brand skin analysis system may calculate the brightness of areas that include the one or more shadows, and may use the brightness calculations to determine a measure of skin texture (e.g., roughness) and skin radiance (e.g., light reflection).

Various features of the Magic Ring® brand skin analysis system are described below. While the invention is not dependent on a particular imaging system, imaging systems for use in the context of the invention preferably have one or more of the features described herein. The compact imaging system consists of a portable image-capturing module that can be positioned on either the left- or the right-hand side of a subject's face. Illumination is provided by a number of 5600-K light-emitting diodes (LEDs) mounted in the imaging module. A high-resolution, complementary-symmetry metal oxide semiconductor (COMS) digital camera, capable of generating at least 2592 (vertical)×1944 (horizontal) effective pixels, is also mounted in the imaging module, and images that it collects or captures are digitally transferred to a computer or computing device. The imaging module further includes a switching circuit and a connector that is configured to communicatively couple to a connector on a charging cradle or base, e.g., when the imaging module is disposed on, attached to or resting in the cradle. Additionally, the imaging module includes a rechargeable battery (e.g., a lithium-ion battery) for powering the digital camera and the LEDs. The rechargeable battery may be recharged and/or discharged when the connector of the imaging module is communicatively connected with the connector of the cradle or base. The camera, LEDs, and battery of the imaging module may be enclosed within a light-blocking housing, a portion of which may extend to be in contact with the skin of a human subject so as to block (or mostly block) ambient light from being captured along with the image of the subject's skin.

The charging cradle or base of the compact imaging system optionally includes the connector, a circuit for administering the charging and de-charging the battery of the imaging module, and an AC or DC inlet via which power to the compact imaging system may be received from a power supply. Additionally, the charging cradle or base optionally includes a communications interface configured to couple to a computer or computing device. For example, the cradle may include a USB or Ethernet port via which a physical cable connected to the computer or computing device may be received. Additionally or alternatively, the cradle may include a wireless interface (e.g., an IEEE 802.11 compatible interface, a Near Field Communications interface (NFC) such as Bluetooth®, or another suitable wireless communications interface) via which the cradle may be in communicative connection to the computer or computing device.

An image captured by the camera may be automatically transferred from the digital camera to the charging base, and then automatically transferred from the charging base to the computer or computing device, e.g., when the connector of the imaging module is in communicative connection with the connector of the charging base or cradle. In some instances, the captured image is transferred based on manually input commands, e.g., commands entered by an operator at a user interface of one of the system components (e.g., at a user interface of the image module, the cradle, and/or the computing device).

Turning now to the computer or computing device of the compact imaging system, in addition to including a communications interface to communicatively couple to the charging cradle or base, the computing device optionally also includes one or more processors, one or more non-transitory, tangible computer-readable storage media or memories, and one or more user interfaces. The one or more computer-readable storage media stores thereon computer-executable instructions that, when executed by the one or more processors, receives a digital image captured by the camera, causes the received image to be displayed on a user interface, allows for masking of the image if desired (either automatically and/or manually via the one or more user interfaces), and allows for automatic and/or manual analysis of the masked image. The instructions, when executed, further cause the results of the analysis to be presented on one or more user interfaces (e.g., at a user interface included in the compact imaging system, and/or at another remote user interface).

Of course, it is understood that other embodiments of the compact imaging system may be utilized in conjunction with any of the techniques, methods and systems described herein. For example, in an embodiment of the Magic Ring® brand skin analysis system, the cradle and the computing device of the compact imaging system are an integral, unitary device. In an embodiment, the imaging module and the cradle are an integral, unitary device. In an embodiment, the imaging module, the cradle and the computing device are an integral, unitary device.

Further, other compact imaging systems other than the Magic Ring® brand skin analysis system may be used in conjunction with any of the techniques, methods and systems described herein. One of many examples of such a compact imaging system may be found in the U.S. Pat. No. 6,571,003 ("the '003 patent"), the entire disclosure of which is incorporated by reference herein. An embodiment of the compact imaging system described in the '003 patent includes an imaging rig which is connected to a computing device for the purpose of acquiring images of human skin to be analyzed. The imaging rig may include positioning equipment, lights, and a digital image generator such as a digital camera, an analog camera connected to a digitizing circuit, a scanner, a video camera, etc. The devices in the imaging rig may be arranged at predetermined distances and predetermined angles relative to one another to maximize the quality of the acquired image.

The computing device of the embodiment of the compact imaging system described in the '003 patent includes a user interface via which an operator may input data, select preferences, and command operation of the compact imaging system. For example, the user interface may present, to the operator, user controls for capturing an image, sizing a captured image, indicating preferences of skin attributes to be analyzed, and initiating the image analysis of the captured image or portions thereof.

The user interface may also present, to the operator, a control for masking a captured image. The term "masking," as used herein, generally refers to determining one or more sub-images of a captured image. A sub-image is a portion of the originally acquired image upon which analysis may be performed, and by analyzing a sub-image instead of the entire acquired image (e.g., by eliminating one or more portions of the acquired image from the analysis process), fewer errors occur. Masking a captured image may be performed manually and/or automatically. Various example techniques of manual and automatic masking are described in the '003 patent, any of which may be utilized in conjunction with the concepts described herein.

Other example techniques of automatic masking are described in U.S. Pat. No. 8,218,862 ("the '862 patent"), the entire disclosure of which is incorporated by reference herein. In an embodiment described in the '862 patent, a mask may be generated based on the locations of anatomical features or landmarks in the image, such as the eyes, nose, eyebrows and lips, which can vary from subject to subject and image to image. As such, masks may be adapted to individual subjects and to different images of the same subjects, while delineating anatomically standardized regions of interest (ROIs), thereby facilitating standardized, reproducible skin analysis over multiple subjects and/or over multiple images of each subject. Moreover, the masks may be limited to skin regions that include uniformly illuminated portions of skin while excluding skin regions in shadow or hot-spot areas that would otherwise provide erroneous feature analysis results.

In addition to masking techniques, the '862 patent also describes techniques for automatically registering a skin mask. Registration of a skin mask enables a delineation of a skin ROI in a first image captured in one imaging modality (e.g., standard white light, UV light, polarized light, multi-spectral absorption or fluorescence imaging, etc.) onto a second image of the ROI captured in the same or another imaging modality so that a comparison of the two images may be performed. For example, the '862 patent describes both rigid and elastic registration techniques that use linear and non-linear spatial transformation techniques.

Similar to the '003 patent, any of the masking and/or registration techniques described in the '862 patent, and indeed, any of the other techniques, concepts, methods and/or apparatuses described in the '862 patent may be used in conjunction with the concepts described herein. Accordingly, computer-executable instructions for performing automatic masking, for allowing manual masking to be initiated and performed, and/or for registering masks (such as described in the '003 patent, described in the '862 patent, or any other suitable techniques) may be stored on a non-transitory, tangible computer-readable storage medium of the computing device of a compact imaging system, and may be executable by a processor of the computing device to cause the compact imaging system to perform the masking and/or registration.

Additionally, computer-executable instructions for image-analysis of a captured image may also be stored on the non-transitory, tangible computer-readable storage medium of the computing device of the compact imaging system, and may be executable by the processor of the computing device to perform the image analysis. In an embodiment, the computing device of the compact imaging system performs one or more of the image analysis algorithms described in the '003 patent, in the '862 patent, and/or described above, either alone or in combination. For example, the image analysis may be performed on one or more sub-images of the captured image. The results of the image-analysis may be displayed on a user interface, and/or may be used to develop one or more current skin quality scores using any of the techniques described above.

Of course, alternative means for determining the current skin feature quality score (block 112) may be utilized other than a compact imaging device, such as the Magic Ring® brand skin analysis system. Current skin feature quality scores also may be determined by visual inspection of the subject, tactical manipulation of the skin, and the like. Alternative evaluation devices include, but are not limited to, New Embedded Skin Diagnosis System from Bomtech Electronics Co., Ltd.; AUTO Skin Diagnostic & Analysis System by KC Technology Co.; ARAMO SG—Skin/Hair Analyzer from Aramhuvis Co., Ltd.; Intelligent Skin Diagnosis System (CBS-900) from Bose View Electronic Co., Ltd.; Hair & Skin Analyzer from Kowa Optics Corp.; A—One Auto UV Scanner Skin Analysis by Parlain Co. Ltd; and Magic Skin Analyzer from Itairen Science & Technology Development Co. Ltd.

In an embodiment, a different current skin feature quality score is determined for each respective skin dimension or feature. These feature-specific current skin feature quality scores are referred to herein as "current skin feature quality scores," and each current skin feature quality score is a quantitative indication (or representation) of the quality or severity of a respective skin feature in the human subject at the time at which the image(s) were captured. For example, a current skin spots score may be indicative of a density of skin spots across the area of the skin surface included in the image(s), and/or indicative of a depth of spectrum constitution of the skin spots. In another example, a current skin tension score may be indicative of an amount of elasticity or firmness of the portions of the skin surface included in the images as indicated by the measured lines, shadows, and areas of brightness.

At block 115, the method 100 may include comparing the current skin feature quality score of the human subject and the predicted skin quality score of the human subject. In an embodiment, the block 115 includes normalizing the current skin quality score and the predicted skin quality score. In another embodiment, the current and the predicted skin quality scores are normalized prior to the block 115. The comparison of the current and the predicted skin quality scores includes, in various aspects of the invention, determining a magnitude of a gap between the normalized scores. The magnitude of the gap may be indicative of a difference between the current skin quality of the human subject and a predicted skin quality of the human subject. For example, if a current skin quality score is equivalent to a predicted skin quality score, the equivalency indicates that the skin quality predicted by the genetic analysis of the human subject mirrors the current skin quality of the human subject. In another example, if the current score of the human subject is lower than the predicted skin quality score, the magnitude of the gap between the scores is indicative of, e.g., how far the current skin quality of the human subject is from the subject's skin potential as predicted by genetic analysis.

In an embodiment, a different gap magnitude may be determined for each skin feature or dimension measured. For example, a magnitude of the gap between a current skin texture quality score and a predicted skin texture score of the human subject may be determined, and a magnitude of the gap between a current skin wrinkles score and a predicted skin wrinkles score of the human subject may be determined. Optionally, the set of gap magnitudes corresponding to the set of skin features are normalized, so that the relative severity of differences across the set of skin dimensions of the human subject may be ascertained and compared. This allows prioritization of skin features to be addressed by a skin care regimen to address the skin feature that has the largest magnitude of the gap between its current and predicted scores.

At block 118, a skin product may be determined based on the magnitude of the gap(s). The skin product may be determined or selected from a group of skin products based on the presence one or more active ingredients suitable for improving skin features associated with a gap between predictive and current scores, or suitable for maintaining skin features where there is no or minimal gap. For example, if at the block 115, the comparison between a current skin spots quality score and a predicted skin spots quality score of the human subject shows that the current skin spots quality lags behind the predicted skin spots quality, then at block 118, a skin product including an active ingredient that has been demonstrated to decrease the intensity of hyper-pigmentation may be selected. However, if at the block 115, the magnitude of the gap between a current skin radiance score and a predicted skin radiance quality score is greater than the magnitude of the gap between current and predicted skin spots score, then a different skin product that includes a radiance-enhancing active ingredient may be selected.

Exemplary Applications of the Methods Described Herein

FIGS. 2A-2C illustrate an example scenario of an application of the method 100 to a particular human subject, who is referred to herein as "SUBJECT." Referring first to FIG. 2A, in this example scenario, SUBJECT provided a buccal mucosa sample, e.g., by swabbing the inside of a cheek (block 100). SUBJECT's sample was genetically analyzed (block 105) to determine the presence or absence of polymorphisms in the selected set of genes MMP1, GPX1, and SOD2, each of which was demonstrated to be associated with skin quality. The genetic analysis of the selected set of genes in SUBJECT's sample (reference 130) identified wild-type GPX1 (rs1050450 was absent), homozygous SNP genotype with respect to MMP1 (rs1799750 found on both copies of the genes), and heterozygous SNP genotype for SOD2 (rs4880 found on one copy of the gene). Respective weightings corresponding to the determined genotypes were accordingly applied (reference 132) to be included in SUBJECT's genetic skin score (block 108).

Next, an image of SUBJECT's nasolabial cheek area was captured by the Magic Ring® brand skin analysis system or other image analysis tool. The Magic Ring® brand skin analysis system automatically performed an image analysis on the captured image to calculate measurements corresponding to the skin texture (e.g., roughness), skin tension, skin wrinkles, skin spots, and skin radiance of SUBJECT's skin, as represented in the captured image. These measurements were then utilized to determine respective current skin feature quality scores (reference 135) that are representative of SUBJECT's current skin quality at the time that the image was captured (block 112). In this example scenario, SUBJECT's current skin feature quality scores are expressed as a percentile with respect to a population, e.g., the control group population. For example, SUBJECT's current wrinkles score of 50 is average, and thus indicates that half of the population has more wrinkles than SUBJECT currently has, and half of the population has less wrinkles than SUBJECT currently has.

FIG. 2B provides the predicted skin features scores for SUBJECT (denoted by the italicized number 138), which were determined by applying a respective predictive equation for each skin feature to SUBJECT's genetic skin score (block 110). In particular, the applied predictive equations used in this example scenario were the equations (1) to (5) discussed above with respect to FIG. 1. In this example scenario, SUBJECT's predicted skin feature quality scores (reference 138) are expressed as a percentile with respect to the control group population. For example, SUBJECT's maximum predicted skin spot risk (based on the analysis of SUBJECT's sample) places her in the 83rd percentile of the control group population, so that if SUBJECT realized her full skin spot potential, 17% of the control group population would have more skin spots than SUBJECT, and 83% of the control group population would have less skin spots than SUBJECT.

In FIG. 2C, a pictorial representation 140 of the five different skin features (dimensions), skin texture, skin tension, skin wrinkles, skin spots, and skin radiance, are simultaneously shown in a superimposed manner to illustrate the comparison between the predicted quality level and the current quality level of each skin dimension or feature of SUBJECT's skin quality. Each different skin dimension score (both predicted and current) are shown on a same axis, so that the magnitude of the gap between the predicted and current scores is readily discernible. For example, the representation 140 shows that SUBJECT's current level of skin spots (e.g., 45) is less than her predicted potential skin spots score (e.g., 83), and thus the respective gap magnitude corresponding to skin spots is 38. Additionally, the representation 140 shows that SUBJECT's current level of skin radiance (e.g., 60) is about equal to her predicted skin radiance score (e.g., 62), thus the respective gap magnitude corresponding to decreased skin radiance is 2 or relatively negligible.

The pictorial representation 140 also illustrates that the different skin feature scores in this example scenario are normalized with respect to one another. That is, the five axes on which the skin feature scores are plotted are normalized with respect to one another. This normalization allows for comparison of relative risk between the different skin features, and may be used to determine which skin products are to be recommended to SUBJECT. For example, out of the five skin features, the largest predicted effect on SUBJECT's skin quality is skin spots (83). Thus, as SUBJECT's current skin spot score is relatively low (45) compared to her predicted skin spot potential, a skin product that includes an active ingredient to prevent skin spot formation may be recommended to SUBJECT so that SUBJECT continues to counteract her genetic tendency to develop skin spots.

In this regard, the invention relates to a method of evaluating the human's skin quality as per described above for the purpose of advising the subject to utilize a skin product to compensate for genetic risk of skin imperfections. In an embodiment, the method involves providing an instructional material to the subject. The instructional material may further advise the subject on the way the method works to establish the magnitude of the gap between the current skin condition and the potential skin condition, and benefits of the skin products.

In another example, a skin product that includes an active ingredient to increase skin radiance may not necessarily be recommended for SUBJECT at this time, as SUBJECT currently appears to be maximizing her potential for skin radiance (as indicated by genetic analysis of her sample). However, at a later time, if SUBJECT's skin is again analyzed to determine an updated current skin radiance score (block 112), and the updated score is less than the score of FIG. 2C, this may indicate that SUBJECT's skin radiance has decreased with respect to the potential allowed by her genetics. At this later time, the skin product including the active ingredient to increase skin radiance may then be identified, selected or recommended for SUBJECT. It is to be noted that the invention is not directed to skin products having any specific formulations or particular compositions (i.e., a particular combination of ingredients). Rather, the invention is directed to advising a subject that has been assessed to have a genome comprising one or more SNPs in one or more skin-related genes correlated to skin features to select skin products intended to address features associated with the polymorphisms.

Accordingly, based on the relative magnitude of the gaps and on the absolute values of predicted skin feature quality scores, one or more skin products (e.g., skin care or cosmetic products) may be selected, identified or recommended for SUBJECT at different instances in time. For example, at each different instance in time, an image analysis of her current skin quality condition at that particular instance in time may be performed and compared to her predicted skin feature quality score to determine an optimized or appropriate skin product for SUBJECT at that particular instance in time. Note that while SUBJECT's current skin feature quality scores may be updated (block 112) at different instances in time to track SUBJECT's skin quality changes or progress, the determination of SUBJECT's predicted skin feature quality score(s) (block 110) need not be repeated, as SUBJECT's genetics do not change over time.

Systems for Assessing Skin Quality

Turning now to FIG. 3, FIG. 3 illustrates an embodiment of a system 200 for assessing the skin quality of a human subject. The system 200 may perform at least a portion of the method 100, in an embodiment. The system 200 may perform at least a portion of another method of assessing human skin quality, in an embodiment.

The system 200 may include a computing device 202 which may be, for example, a computer, a server, a plurality of networked computing devices having a logical appearance of a single computing device, a plurality of cloud computing devices, etc. Accordingly, for ease of discussion only and not for limitation purposes, the computing device 202 is referred to herein using the singular tense, although in some embodiments the computing device 202 may include more than one physical computing device. In an embodiment, the computing device 202 may be physically located at a point of consumer contact (e.g., cosmetics counter), and may be directly accessible by technician. In an embodiment, the computing device 202 may be a web server that is remotely located from the cosmetics counter, but is communicatively accessible to a technician at the cosmetics counter, e.g., via a network, a website, a portal, or the like.

The computing device 202 may include a program memory 208, a processor 210 (may be called a controller, a microcontroller, or a microprocessor), a random-access memory (RAM) 212, and an input/output (I/O) circuit 215, all of which may be interconnected via an address/data bus 218. The program memory 208 may comprise one or more tangible, non-transitory computer-readable storage media or devices, in an embodiment. The one or more tangible, non-transitory computer-readable storage media or devices may be configured to store computer-readable instructions 220 that, when executed by the processor 210, cause the computing device 202 to implement the method 100 or another method of assessing the skin quality of a human subject.

The instructions 220 may include a first portion 220A for determining a predicted skin feature quality score of a human subject (e.g., of a cosmetics client or customer). For ease of discussion, the instructions 220A are referred to herein as a "skin quality predictor 220A," and in an embodiment, the skin quality predictor 220A may perform at least block 110 of the method 100. In an embodiment, the skin quality predictor 220A performs block 108 of the method 100.

Additionally or alternatively, the instructions 220 may include a second portion 220B for determining a gap between a predicted skin feature quality and a current skin feature quality of the human subject. For ease of discussion, the instructions 220B are referred to herein as a "skin quality gap evaluator 220B," and in an embodiment, the skin quality gap evaluator 220B may perform at least block 115 of the method 100. For example, the skin quality gap evaluator 220B may determine a magnitude of a gap between a predicted skin quality value and a current skin quality value, and may cause an indication of the gap magnitude to be presented at a user interface 250A and/or at a user interface 250B.

The computing device 202 may be configured or adapted to access or receiving data from one or more data storage devices 222. For example, the instructions 220 may be executable by the processor 210 to access the one or more data storage devices 222 or to receive data stored at the data storage devices 222. Additionally or alternatively, one or more other sets of computer-executable instructions 258 may be executable by the processor 210 to access or receive data from the one or more data storage devices 222.

The one or more data storage devices 222 may comprise, for example, one or more memory devices, a data bank, cloud data storage, or one or more other suitable data storage devices. In the embodiment illustrated in FIG. 3, the computing device 202 is shown as being configured to access or receive information from the one or more data storage devices 222 via a network or communications interface 228 that is coupled to a link 230 in communicative connection with the one or more data storage devices 222. The link 230 in FIG. 3 is depicted as a link to one or more private or public networks 232 (e.g., the one or more data storage devices 222 are remotely located from the computing device 202), although this is not required. The link 230 may include a wired link and/or a wireless link, or may utilize any suitable communications technology.

In an embodiment (not shown), at least one of the one or more data storage devices 222 is included in the computing device 202, and the processor 210 of the computing device 202 (or the instructions 220, 258 being executed by the processor 210) accesses the one or more data storage devices 222 via a link comprising a read or write command, function, primitive, application programming interface, plug-in, operation, or instruction, or similar.

The one or more data storage devices 222 may include one physical device, or the one or more data storage devices 222 may include more than one physical device. The one or more data storage devices 222, though, may logically appear as a single data storage device irrespective of the number of physical devices included therein. Accordingly, for ease of discussion only and not for limitation purposes, the data storage device 222 is referred to herein using the singular tense.

The data storage device 222 may be configured or adapted to store data related to the system 200. For example, the data storage device 222 may be configured or adapted to store one or more predictive equations 235a-235n, each of which may correspond to a different skin quality feature or dimension, e.g., skin texture, skin spots, skin radiance, skin wrinkles, skin tension, or other skin quality feature or dimension. In an embodiment, the predictive equations 235a-235n include at least the equations (1) to (5) discussed above with respect to FIG. 1.

In an embodiment, the skin quality predictor 220A is configured or adapted to determine the predicted skin quality score (block 110) of the human subject based on one or more of the predictive equations 235a-235n. The skin quality predictor 220A may query the data storage device 222 for the one or more of the predictive equations 235a-235n as needed, and/or the one or more predictive equations 235a-235n may be delivered to or downloaded to the computing device 202 a priori.

In FIG. 3, a skin measurement provider 255 may perform an image analysis on an image of the skin surface of a human subject to determine the plurality of measurements corresponding to a selected set of skin features. In an embodiment, the skin measurement provider 255 is configured to both capture the image and perform the image analysis. In an embodiment, the skin measurement provider 255 is configured to perform the image analysis to determine the plurality of measurements, and to cause the plurality of measurements to be delivered to the computing device 202.

In an embodiment, the skin measurement provider 255 may be remotely located from the computing device 202, and may cause the determined measurements to be transmitted to the computing device 202 using the network 232 and the network interface 228 so that the skin 20 quality gap evaluator 220B may determine a current skin quality score for the human subject (block 112). In an embodiment, the skin measurement provider 255 may be directly (e.g., locally) connected to the computing device 202 via the network interface 228. In an example, the skin measurement provider 255 may be a Magic Ring® brand skin analysis system that is locally or remotely connected to the computing device 202. In an embodiment (not shown), at least a portion of the 25 skin measurement provider 255 is integral with the computing device 202.

In an embodiment, in addition to determining the plurality of measurements corresponding to a selected set of skin features, the skin measurement provider 255 may also determine the current skin quality score of the human subject (block 112) of the human subject, and may cause the current skin quality score of the human subject to be transmitted to the skin quality gap evaluator 220B of the computing device 202.

Turning again to the computing device 202, while the skin quality predictor 220A is shown as a single block in FIG. 3, it will be appreciated that the skin quality predictor 220A may include a number of different programs, modules, routines, and sub-routines that may collectively cause the computing device 202 to implement the skin quality predictor 220A. In an embodiment, the skin quality predictor 220A is executable by the processor 210 to cause the computing device 202 to obtain an indication of a presence or absence of one or more polymorphisms of a set of human genes (e.g., MMP1, SOD2, and GPX1) from the human subject. For example, the indication of the presence or absence of the one or more polymorphisms of the set of human genes may be obtained via the user interface 250A, the user interface 250B, and/or the communications interface 228. The presence or the absence of the one or more polymorphisms may have been determined from an analysis of nucleic acid from a biological sample from a human subject, as described elsewhere herein. Further, the presence or absence of the one or more polymorphisms may be associated with set of skin features, and the set of skin features may be included in a set of skin features indicative of skin quality in humans. In an embodiment, the set of skin features includes at least two of skin wrinkles, skin spots, a decrease in skin tension, a decrease in skin radiance, or an increase in the roughness of skin texture.

The skin quality predictor 220A may be further executable by the processor 210 to determine, for each polymorphism whose presence or absence was indicated in the obtained indication, a respective strength of correlation of the presence or absence of the each polymorphism to each skin feature included in the set of skin features. The skin quality predictor 220A may be further executable by the processor 210 to determine a predicted skin quality value indicative of the predicted skin quality of the human subject. The predicted skin quality value may be determined, for example, based on the respective strengths of correlation and based on a plurality of values corresponding to the set of skin features indicative of the skin quality of a plurality of other human subjects. An age range of the plurality of human subjects may span an expected human lifetime, or at least one decade, at least two decades, at least three decades, at least four decades, or at least five decades, for example.

In an embodiment, the skin quality predictor 220A may be further executable by the processor 210 to cause the predicted skin quality value to be presented at a user interface. Alternatively, the other instructions 258 may be executable by the processor 210 to cause the predicted skin quality value to be presented at a user interface.

Similarly, while the skin quality gap evaluator 220B is shown as a single block, it will be appreciated that the other instructions for evaluating a skin quality gap 220B may include a number of different programs, modules, routines, and sub-routines that may collectively cause the computing device 202 to implement the other instructions for evaluating a skin quality gap evaluator 220B. In an embodiment, the skin quality gap evaluator 220B may be executable by the processor 210 to cause the computing device 202 to receive first data that includes at least one indication of the presence or absence, in a biological sample from the human subject, of at least one polymorphism in a set of human genes (e.g., MMP1, SOD2, and GPX1). For example, the first data may be received via the user interface 250A, the user interface 250B, or the network interface 228. The skin quality gap evaluator 220B may be further executable by the processor 210 to cause the computing device 202 to determine a value indicative of the predicted skin quality of the human subject, where the predicted skin quality value of the human subject is determined based on the first data and on a correlation of the presence or absence of the at least one polymorphism to a set of skin features indicative of skin quality.

Additionally, the skin quality gap evaluator 220B may be executable by the processor 210 to cause the computing device 202 to receive second data including a value indicative of the current skin quality of the human subject. For example, the second data may be received via the user interface 250A, the user interface 250B, or the network interface 228. The current skin quality value may have been determined based on an automatic image-analysis of an image of a portion of the skin surface of the human subject, and the automatic image-analysis may be configured to determine one or more measurements corresponding to the set of skin features of the portion of the skin surface to determine the current skin quality value. The skin quality gap evaluator 220B may be further executable by the processor 210 to cause the computing device 202 to determine, based on the predicted skin quality value and the current skin quality value, a magnitude of a gap between the predicted skin quality and the current skin quality of the human subject.

In an embodiment, the skin quality gap evaluator 220B may be executable by the processor 210 to cause an indication of the gap magnitude to be presented at a user interface, such as the user interface 250A and/or the user interface 250B. Alternatively, the other instructions 258 may be executable by the processor 210 to cause the indication of the gap magnitude to be presented at a user interface, such as the user interface 250A and/or the user interface 250B.

In various embodiments, the computing device 202 includes other instructions 258 corresponding to assessing the skin quality of a human subject. For example, the other instructions 258, when executed by the processor 210, may cause the computing device 202 to identify or determine a skin product corresponding to the comparison of the predicted skin quality score(s) and the current skin quality score(s). In an embodiment, at least a portion of the instructions 220 for assessing skin quality of a human subject and at least a portion of the other instructions 258 may be an integral set of instructions.

It should be appreciated that although only one processor 210 is shown, the computing device 202 may include multiple processors 210. Additionally, although the I/O circuit 215 is shown as a single block, it should be appreciated that the I/O circuit 215 may include a number of different types of I/O circuits. Similarly, the memory of the computing device 202 may include multiple RAMs 212 and multiple program memories 208. Further, while the instructions 220 for opening a new financial account and the other instructions 258 are shown being stored in the program memory 208, the instructions may additionally or alternatively be stored in the RAM 212 or other local memory (not shown).

The RAM(s) 212 and program memories 208 may be implemented as semiconductor memories, magnetically readable memories, chemically or biologically readable memories, and/or optically readable memories, or may utilize any suitable memory technology. The computing device 202 may also be operatively connected to the network 232 via the link 230 and the I/O circuit 215. The network 232 may be a proprietary network, a secure public internet, a virtual private network or some other type of network, such as dedicated access lines, plain ordinary telephone lines, satellite links, combinations of these, etc. Where the network 232 comprises the Internet, data communications may take place over the network 232 via an Internet communication protocol, for example.

Additionally, the user interface 250 may be integral to the computing device 202 (e.g., the user interface 250A), and/or the user interface may not be integral with the computing device 202 (e.g., the user interface 250B). For example, the user interface 250 may be a remote user interface 250B at a remote computing device, such as a web page or a client application. In any event, the user interface 250 may effectively be a communications interface between the computing device 202 and a user.

Compositions and Personal Care Products

In some embodiments, a skin product (i.e., a skin care composition) is selected or recommended to the subject based on the genetic analysis, optionally in combination with the image analysis. The skin product is selected based, at least in part, on the presence of an active ingredient that improves or maintains a skin feature selected from the group consisting of skin wrinkles, skin texture, skin radiance, skin spots, and skin tension. For example, the skin product, in various aspects, includes an active ingredient that maintains or promotes collagen production, reduces or increases sebum production, renders fine lines and/or wrinkles less noticeable, enhances skin hydration or suppleness, improves skin texture and smoothness (e.g., reduces scaliness), lessens or prevents discoloration, improves skin color, increases skin volume and firmness, and/or improves or maintains skin elasticity. In various aspects, the skin product contains niacinamide. It will be appreciated that the skin feature (imperfection) need not be completely prevented or eradicated to achieve a desirable response. Any degree of improvement of one or more skin features is contemplated. Similarly, any delay in the appearance of one or more unwanted skin features is contemplated.

The skin product may be part of a hygiene routine relating to the skin. In one aspect, the skin product is formulated as, e.g., facial cleanser, moisturizer, lotion (e.g., clarified lotion), cream (such as eye cream and/or lip cream), facial skin cosmetic (such as blusher and highlighter), eye cosmetic (such as eye shadow, eye brow color, and eye liner), lip cosmetic (such as lip rouge), foundation, concealer, wrinkle soothing serum, skin facial mask, sunscreen, emulsion, oil, milk, pomade, solution, spray, aerosol, powder, foam, gel (such as skin gel, eye gel, and/or lip gel), serum, stick, paste, or other skin products or treatment. In one embodiment, the composition is intended to be left on the skin for some esthetic, prophylactic, therapeutic or other benefit (i.e., a "leave-on" composition).

In some embodiments, the skin product comprises one or more active components selected from the group consisting of a vitamin, a vitaminoid, a mineral, a trace element, an amino acid, a phytocompound, an antioxidant, an algae, and a coenzyme. Examples of such components and typical dosage ranges are listed below in Tables 2 to 7.

TABLE 2

Vitamins/Vitaminoids (Antioxidants)

| Compound | Dosage range |
|---|---|
| L-Ascorbic Acid (Vitamin C) | 200-1,000 mg |
| Bioflavanoids (Aserola-, Citrus-) | 200-250 mg |
| Ascorbylpalmitat (lipid-soluble Vitamin C) | 20-50 mg |
| d-Alpha-Tocopherol (Vitamin E) | 50-400 mg |
| Mixed alpha-, beta-, gamma-, delta-Tocopherols/Tocotrienols | 50-200 mg |
| Mixed Carotinoids | 10 mg |
| Lycopene | 2-4 mg |
| Zeaxanthin | 2.5-5 mg |
| Lutein | 5-10 mg |
| Vitamin A (Palmitate) | 2,500-5,000 IU |
| Cholecalciferol (Vitamin D) | 200-400 IU |
| Vitamin K1/K2 | 2-5 mg/0.5-1 mg |
| Alpha Lipoic Acid (ALA) | 100-400 mg |
| Ubiquinol (Coenzyme Q10) | 30-200 mg |
| Oligomer proanthocyanides, OPC | 25-50 mg |

TABLE 3

B-Vitamins

| Compound | Dosage Range |
|---|---|
| Thiamin (Vitamin B1) | 10-50 mg |
| Riboflavin (Vitamin B2) | 10-50 mg |
| Niacin (Vitamin B3) | 10-50 mg |
| Panthothenic acid (Vitamin B5) | 100-200 mg |
| Pyridoxin (Vitamin B6) | 10-50 mg |
| Pyridoxalphosphate (Activated Vitamin B6) | 1-4 mg |
| Cyanocobalamin (Vitamin B12) | 4,000-1,000 μg |
| Methylbalamin (Vitamin B12) | 100-1,000 μg |
| Folic acid | 400-800 μg |
| Biotic | 500-1,000 μg |
| Trimethylglycine (Betain) | 150-250 mg |

TABLE 4

Amino acids

| Compound | Dosage Range |
|---|---|
| L-proline | 250-500 mg |
| L-tyrosine | 250-500 mg |
| L-lysine | 250-500 mg |
| L-Carnitine | 250-500 mg |
| N-acetyl-L-cysteine | 250-500 mg |
| Taurine | 250-500 mg |

TABLE 5

Lipids

| Compound | Dosage Range |
|---|---|
| Eicosapentaenoic acid (EPA) | 500-750 mg |
| Docosahexaenoic acid (DHA) | 300-500 mg |
| Alpha-linolenic acid | 1,000-2,000 mg |

TABLE 5-continued

Lipids

| Compound | Dosage Range |
| --- | --- |
| Gamma-linolenic acid | 100-200 mg |
| Cholina | 50-100 mg |
| Phosphatidylcholine | 100-150 mg |
| Inositol | 100-200 mg |
| Soy lecithin (99% oil free, 97% phosphatides) | 500-1,000 mg |

TABLE 6

Trace Elements

| Compound | Dosage Range |
| --- | --- |
| Zinc | 10-30 mg |
| Selan (from yeast or an organic as sodium selanite) | 50-200 g |
| Boron | 1-3 mg |
| Calcium | 200-300 mg |
| Magnesium | 150-250 mg |
| Chromium (e.g., chromium polynicotinate) | 100-200 μg |
| Molybdenum (e.g., sodium molybdate) | 50-100 μg |
| Vanadium (e.g., sodium methavanadate) | 5-10 μg |

TABLE 7

Phytocompounds (Vegetable and/or fruit complex)

| Compound | Dosage Range |
| --- | --- |
| Resveratrol | 4-5 mg |
| Indole-2-carbinol (13C) | 100-200 mg |
| Bioflavanoids (Acerola-, Citrus-) | 200-250 mg |
| Quercetin | 50-300 mg |
| Pycnogenol ® | 10-25 mg |
| Saw palmetto CO2 extract | 150-300 mg |
| Nettle leaf extract | 500-1,000 mg |
| Bilberry | 25-100 mg |
| Green tea extract | 100-200 mg |
| Grapeseed extract | 10-25 mg |
| Oligomer proanthocyanidinines | 25-50 mg |
| Milk thistle extract | 50-100 mg |
| Raspberry extract | 50-120 mg |
| Acerola juice powder | 100-300 mg |
| Broccoli concentrate | 250-500 mg |
| *Ginkgo biloba* extract | 50-120 mg |
| Curcumin | 500-650 mg |
| Soy estract | 150-300 mg |
| *Spirulina* (blue green algae) | 100-200 mg |

A skin product comprising one or more of the components listed in the above tables is specifically contemplated. In some embodiments, the skin product comprises a niacin-containing compound. In some embodiments, the cosmetic composition comprises niacinamide. The above materials are provided as examples. Of course, many other ingredients may be incorporated into a skin product (e.g., a cosmetic composition). Additional ingredients include but are not limited to gamma-linolenic acid (GLA), coenzyme Q10, vitamin F liposomes, hyaluronic acid, as well as oils including jojoba oil and macadamia nut oil.

The invention may be more readily understood by reference to the following examples, which are given to illustrate the invention and not in any way to limit its scope.

EXAMPLES

This example demonstrates the significant relationship between three SNPs and five skin features.

Skin related single nucleotide polymorphisms (SNPs) of MMP1 (rs1799750; GAAATTGTAGTTAAATAATTA-GAAAG[-/G]ATATGACTTATCTCAAATCAATCCA (SEQ ID NOs: 1 and 2), SOD2 (rs4880; CAGCACCAGCA-GGCAGCTGGCTCCGG[C/T]TTTGGGG-TATCTGGGCTCCAGGCAG (SEQ ID NOs: 3 and 4) and GPX1 (rs1050450; CATCGAAGCCCTGCTGTCT-CAAGGGC[C/T]CAGCTGTGCCTAGGGCGCCCCTCCT (SEQ ID NOs: 5 and 6) genotypes were analyzed among two different Japanese female groups aged 28 to 76 (n=235), of which 115 Japanese females had used a skin care regimen for longer than three years (i.e., the "long term user group") and 120 Japanese females had not used the specific skin care regimen (i.e., the "control group"). "Risk" associated with development of a skin feature was assigned to each genotype: wild-type (i.e., absence of polymorphism on both genes) was assigned low risk, heterozygous (i.e., the polymorphism present on only one copy of the gene) was assigned medium risk, and homozygous (i.e., the polymorphism present on both copies of the gene) was assigned high risk. The genotype and risk associated with the presence of each SNP is provided in Table 8 below:

TABLE 8

Genotype and Risk of Control and Long Term User Groups

| | | | Genotype and Risk | | |
| --- | --- | --- | --- | --- | --- |
| Gene | dnSNP ID | SEQ ID NO: | Wild (Low Risk) | Hetero (Medium Risk) | Homo (High Risk) |
| MMP1 | rs1799750 | 1 and 2 | Del/Del | Ins/Del | Ins/Ins |
| SOD2 | rs4880 | 3 and 4 | 16Ala/16Ala | 16Ala/16Val | 16Val/16Val |
| GPX1 | rs1050450 | 5 and 6 | 200Pro/200Pro | 200Pro/200Leu | 200Leu/200Leu |

From the genotype analysis performed on the long term user group and the control group, it was determined that 93.1% of the population tested had risk associated with MMP1 (Hetero/Homo), 77.0% for SOD2 (Homo), and 13.4% for GPX1 (Hetero/Homo), and the frequency of each genotype was consistent in both the long term user group and the control group.

Image analysis of the face of the members of the long term user group and the control group was then performed using a compact imaging system (Magic Ring® brand skin analysis system) to assess the subjects' current skin condition. The compact imaging system is described in Miyamoto K. et al., Skin Res. Tech., 19:e525-e531, 2013, the disclosure of which is incorporated herein by reference in its entirety, and above. The Magic Ring® brand skin analysis system was used to evaluate five skin features: skin lines/wrinkles, skin spots, skin texture, skin radiance, and skin firmness. The system was used as described in Miyamoto, supra. For example, an image-analysis algorithm stored at and executed by the computing device was used to detect and quantify facial lines and their direction. The region of interest was defined as the cheek and nasolabial cheek region; this was analyzed by the image-analysis algorithm to quantify the total numbers and lengths of facial lines that were longer than 3 mm and wider than 0.12 mm Except for the selection of the region of the skin to be assessed, image analysis was performed automatically and the results were stored in the computer as binary images with facial lines for later retrieval and analysis. First, the total area of facial lines (number of pixels) in the region of interest was calculated. Then the direction of each facial line was measured to determine the mean direction of the facial lines. The direction of the facial lines was measured by fitting a Gaussian distribution to a power spectrum, which was calculated by using a facial line overlay image. The spectrum was smoothed to reduce narrow peaks and the line direction angle (the center of the Gaussian function) was then calculated. The special distance of the facial line was calculated by using the following expression:

Spatial distance of facial line $\sin(\theta 1) \times d$, where $\theta 1$ is the mean direction of the facial lines and d is their total area.

This information was simplified by representing it as a single parameter called the Ageless Vector, which corresponds to the angle between the horizontal and the vector product of the mean direction of the facial lines and their total area: Ageless Vector $\theta$=a tan (spatial distance of facial line)$\times 180/\pi$.

The Ageless Vector increases with increasing number of facial lines and their increasing downward angle.

Correlation of Skin DNA and Skin Parameters

Figure 4A:
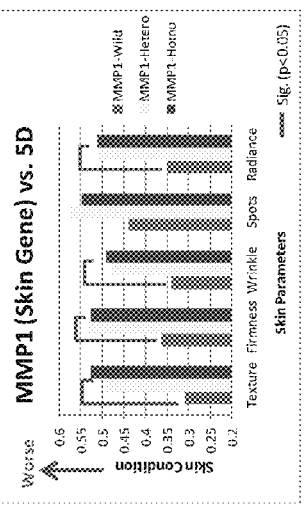
FIG. 4A-4C are bar graphs illustrating severity (y-axis) of skin features (x-axis) (analyzed by image analysis) associated with polymorphisms in MMP1 (FIG. 4A), SOD2 (FIG. 4B) and GPX1 (FIG. 4C) in subjects that had not used a specific skin care regimen prior to the study. The severity score of the y-axis was fit from 0 (best skin condition) to 1.0 (worst skin condition) across the tested skin parameters. For each skin feature, the severity associated with wild-type genotype (MMP1 and GPX1), heterozygous polymorphism (MMP1, SOD2, and GPX1), and homozygous polymorphism (MMP1 and SOD2) is depicted by the bars (oriented left to right, respectively, in the graphs). The identified polymorphisms are correlated with skin texture, decreased skin firmness, skin spots, skin wrinkles, and decreased skin radiance.
Figure 4B:
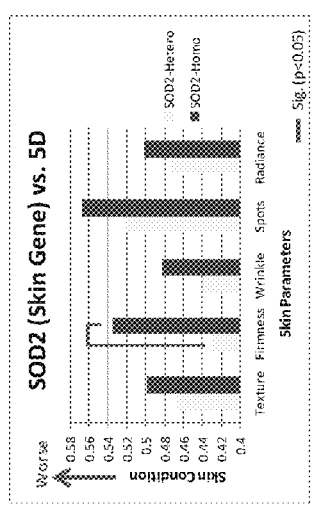
Figure 4C:
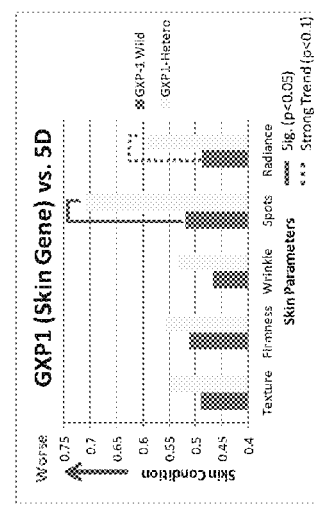

Comparison of the skin DNA results and the image analysis showed a clear relationship between the presence of MMP1, SOD2, and GPX1 polymorphisms and skin texture, skin wrinkles/lines, skin spots, skin brilliance, and skin firmness. Representative results are provided in FIG. 4A-4C. The correlation is stronger with increased age, as illustrated in FIG. 5.

The skin DNA results were normalized to the image analysis data by regression analysis to generate prediction algorithms to predict skin firmness, skin texture, skin wrinkles, skin spots and skin radiance of the subjects tested based on the skin DNA scores. The predicted models showed a significant relationship with the actual skin measurement parameters obtained by the image analysis. See FIGS. 6A-6E. The predicted models were adjusted to fit a 0-100 scale for better comparison among the skin parameters. The score associated with most severe state of a particular skin condition was assigned 0, the score associated with the best state of a skin condition was assigned 100, and the score associated with average skin condition for a tested parameter was assigned 50. The adjusted models are useful for evaluating current skin quality and formulating recommendations to improve skin quality, e.g., rectify a gap between the results of predictive modeling via skin DNA analysis (i.e., skin potential) and the results of the image analysis (i.e., current skin quality), as well as prioritize skin parameters for improvement. For example, subjects may be segmented into groups by overlaying the image analysis score (e.g., represented as a 0-100 scale, with higher values representing more desired characteristics) and predicted skin DNA score (e.g., represented as a percentage, with higher values representing a better skin DNA condition (i.e., lower risk)) for each skin parameter: (a) higher score (>50) in both image analysis and predicted skin DNA score; (b) higher image analysis score (>50) and lower predicted skin DNA score (<50); (C) lower image analysis score (<50) and higher predicted skin DNA score (>50); and (d) lower score (<50) in both image analysis and predicted skin DNA score. A particular skin care regimen may be recommended based on the subject's classification.

Figure 7A:
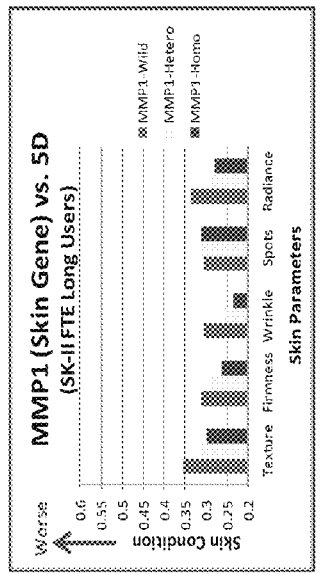
FIG. 7A-7C are bar graphs illustrating severity (y-axis) of skin features (x-axis) associated with polymorphisms in MMP1 (FIG. 7A), SOD2 (FIG. 7B) and GPX1 (FIG. 7C) in subjects that had used a specified skin care regimen for three years prior to the study. For each skin feature, the severity associated with wild-type genotype (MMP1 and GPX1), heterozygous polymorphism (MMP1, SOD2, and GPX1), and homozygous polymorphism (MMP1 and SOD2) is depicted by the bars (oriented left to right, respectively, in the graphs). The identified polymorphisms are correlated with skin texture, decreased skin firmness, skin spots, skin wrinkles, and decreased skin radiance.
Figure 7B:
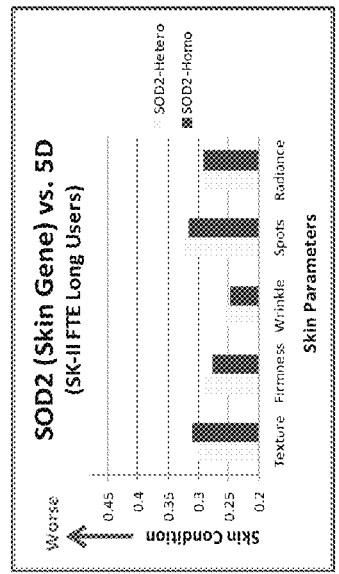
Figure 7C:
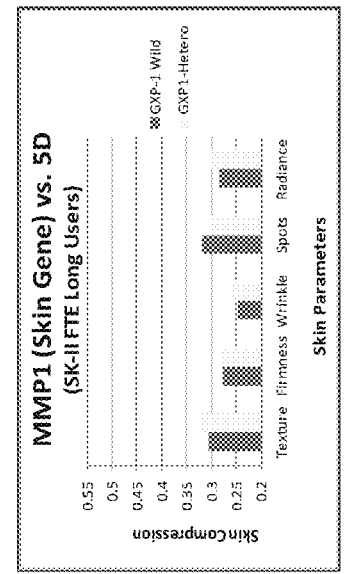

Among the "control" group, there was a clear relationship between polymorphisms in MMP1, SOD2, and GPX1 and the five visible skin appearances examined (i.e., skin texture, skin firmness, skin wrinkles, skin spots, and skin radiance). MMP1 influenced multiple skin parameters (i.e., skin texture, skin firmness, skin wrinkles and skin radiance), while GPX1 and SOD2 demonstrated specific impact on the skin parameters skin spots, skin radiance and skin firmness. See FIG. 4A-C. Results indicated that the relationships between genetic skin scores and the respective skin parameters became more correlated after the subject reached age 40. See FIG. 5. The correlation between genetic skin scores and corresponding skin features was not as strong for long time users of a skin care regimen. See FIG. 7A-7C. This indicates that long term users of skin care products can overcome their genetic skin "potential."

All publications and patents mentioned herein are hereby incorporated by reference in their entirety as if each individual publication or patent was specifically and individually indicated to be incorporated by reference.

Although the foregoing text sets forth a detailed description of numerous different embodiments, it should be understood that the scope of the patent is defined by the words of the claims set forth at the end of this patent. The detailed description is to be construed as exemplary only and does not describe every possible embodiment because describing every possible embodiment would be impractical, if not impossible. Numerous alternative embodiments could be implemented, using either current technology or technology developed after the filing date of this patent, which would still fall within the scope of the claims.

Thus, many modifications and variations may be made in the techniques and structures described and illustrated herein without departing from the spirit and scope of the present claims. Accordingly, it should be understood that the methods and systems described herein are illustrative only and are not limiting upon the scope of the claims.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of assessing the skin quality of a human subject, the method comprising:

determining the presence or absence of polymorphisms in MMP1, SOD2, and GPX1 in a biological sample from the human subject to provide a genetic skin score;

determining a predicted skin feature quality score corresponding to a skin feature selected from the group consisting of skin wrinkles, skin spots, decreased skin tension, decreased skin radiance, and skin texture roughness by applying a predictive equation corresponding to the skin feature to the genetic skin score, wherein the predictive equation corresponds to the skin feature and is determined by a regression analysis of data obtained from a control group comprising members whose ages span at least two decades, the data comprising:

(i) a genetic skin score of each member of the control group, and (ii) a plurality of measurements corresponding to each member of the control group, wherein the plurality of measurements are associated with the skin feature and calculated from an image analysis of a skin surface of each member of the control group, and wherein the predicted skin feature quality score is representative of a risk of the human subject developing the skin feature;

determining a current skin feature quality score of the human subject from image analysis of an image of a skin surface of the human subject, the current skin feature quality score corresponding to the skin feature; and determining a magnitude of a gap between the predicted skin feature quality score and the current skin feature quality score.

2. The method of claim 1, wherein the polymorphisms are rs1799750, rs4880, and rs1050450.

3. The method of claim 1, wherein the image analysis is configured to determine the plurality of measurements based on at least one of:
- a line on the skin surface, the line determined based on a shadow in the image;
- a brightness of an area of the shadow;
- a length and a width of the line;
- a horizontal-to-vertical ratio of the line;
- a linearity of the line;
- a circularity of the line;
- a total area of the line;
- a mean direction of the line;
- a quantity of lines detected on the skin surface;
- a depth of spectrum constitution of one or more portions of the image;
- a size of the one or more portions having a particular depth of spectrum constitution;
- a size of an image of one or more sebaceous glands captured in the image of the skin surface; or
- an angle of the one or more sebaceous glands captured in the image of the skin surface.

4. The method of claim 1, wherein the method further comprises counseling the human subject with respect to a skin product suitable for improving the appearance of the skin feature, the skin product selected based on the magnitude of the gap.

5. The method of claim 1, wherein the method comprises determining a respective predicted skin feature quality score for each skin feature included in the group of skin features.

6. The method of claim 5, further comprising:
determining, based on image analysis of an image of a skin surface of the human subject, a respective current skin feature quality score corresponding to each skin feature included in the group of skin features; and
determining a respective magnitude of a respective gap between the predicted skin feature quality score and the current skin feature quality score for each skin feature included in the group of skin features.

7. The method of claim 6, further comprising:
identifying a skin feature associated with the largest gap magnitude of the determined gap magnitudes; and
identifying a skin product suitable for improving the appearance of the specific skin feature.

8. The method of claim 1, further comprising:
determining a subsequent skin feature quality score of the human subject from a subsequent image analysis of a skin surface of the human subject at a time point after the image analysis of claim 1; and
determining a magnitude of a gap between the predicted skin feature quality score and the subsequent skin feature quality score of the human subject.

9. The method of claim 1, further comprising applying a skin product comprising an active ingredient suitable for improving the skin feature.

10. A system for assessing the skin quality of a human subject, the system comprising:
at least one processor;
an interface; and
at least one tangible, non-transitory computer readable storage medium storing computer executable instructions that, when executed by the at least one processor, cause the system to perform the method as claimed in any of claims 1 to 9.

11. A system for determining a gap between a predicted skin quality and a current skin quality of a human subject, the system comprising:
at least one processor;
at least one communications interface; and
at least one tangible, non-transitory computer-readable storage medium having stored thereon a skin quality gap evaluator, the skin quality gap evaluator including computer executable instructions that, when executed by the at least one processor, cause the system to:
receive, via the at least one communications interface, first data including at least one indication of the presence or absence, in a biological sample from the human subject, of at least one polymorphism in a set of human genes;
determine a value indicative of the predicted skin quality of the human subject, the predicted skin quality value of the human subject determined based on the first data and on a correlation of the presence or absence of the at least one polymorphism to a set of skin features indicative of skin quality;
receive, via the at least one communications interface, second data including a value indicative of the current skin quality of the human subject, the current skin quality value determined based on an automatic image-analysis of an image of a portion of the skin surface of the human subject, wherein the automatic image-analysis is configured to determine a measurement corresponding to the set of skin features of the portion of the skin surface;
determine, based on the predicted skin quality value and the current skin quality value, a magnitude of a gap between the predicted skin quality and the current skin quality of the human subject; and
cause an indication of the gap magnitude to be presented at a user interface.

12. The system of claim 11, wherein a weight of the correlation of the presence or absence of the at least one polymorphism is indicative of one of a wild genotype, a heterozygous genotype, or a homozygous genotype.

13. The system of claim 11, wherein the presence or absence of each polymorphism in the set of human genes is determined, by regression analysis, to affect at least one of the set of skin features.

14. A method of determining, based on a set of skin features corresponding to skin quality of humans, a gap between a predicted skin quality and a current skin quality of a human subject, the method comprising:
(a) analyzing at least one skin surface of the human subject to determine at least one measurement indicative of the current skin quality of the human subject, wherein the at least one measurement corresponds to at least one skin feature of the set of skin features; and
(b) determining, by a computing device and based on the at least one measurement, a magnitude of a gap between the current skin quality of the human subject and the predicted skin quality of the human subject, the predicted skin quality of the human subject determined based on a presence or absence of at least one polymorphism identified in nucleic acid from a biological sample from the human subject,
wherein:
each polymorphism of the at least one polymorphism is correlated with affecting one or more skin features of the set of skin features corresponding to skin quality, and
the set of skin features corresponding to skin quality includes at least one of skin wrinkles, skin texture roughness, skin spots, decreased skin radiance, or decreased skin tension.

\* \* \* \* \*

SEQUENCE LISTING

<160> NUMBER OF SEQ ID NOS: 6

<210> SEQ ID NO 1
<211> LENGTH: 51
<212> TYPE: DNA
<213> ORGANISM: Homo sapiens

<400> SEQUENCE: 1
gaaattgtag ttaaataatt agaaagatat gacttatctc aaatcaatcc a        51

<210> SEQ ID NO 2
<211> LENGTH: 52
<212> TYPE: DNA
<213> ORGANISM: Homo sapiens

<400> SEQUENCE: 2
gaaattgtag ttaaataatt agaaaggata tgacttatct caaatcaatc ca       52

<210> SEQ ID NO 3
<211> LENGTH: 52
<212> TYPE: DNA
<213> ORGANISM: Homo sapiens

<400> SEQUENCE: 3
cagcaccagc aggcagctgg ctccggcttt ggggtatctg ggctccaggc ag       52

<210> SEQ ID NO 4
<211> LENGTH: 52
<212> TYPE: DNA
<213> ORGANISM: Homo sapiens

<400> SEQUENCE: 4
cagcaccagc aggcagctgg ctccggtttt ggggtatctg ggctccaggc ag       52

<210> SEQ ID NO 5
<211> LENGTH: 52
<212> TYPE: DNA
<213> ORGANISM: Homo sapiens

<400> SEQUENCE: 5
catcgaagcc ctgctgtctc aagggcccag ctgtgcctag ggcgcccctc ct       52

<210> SEQ ID NO 6
<211> LENGTH: 52
<212> TYPE: DNA
<213> ORGANISM: Homo sapiens

<400> SEQUENCE: 6
catcgaagcc ctgctgtctc aagggctcag ctgtgcctag ggcgcccctc ct       52